United States Patent [19]

Olson et al.

[11] Patent Number: 5,307,976

[45] Date of Patent: May 3, 1994

[54] LINEAR STAPLING MECHANISM WITH CUTTING MEANS

[75] Inventors: Todd Olson, Loveland; Dan Meiser, Oxford; Gary Steed, Cleves; Eric Huffman, Loveland; Matthew Otten, Cincinnati; Ronald VanOverloop, West Chester; Darrel Powell, Cincinnati; Thomas Knodell, Loveland; Edward Rhad, Fairfield; Ralph Chen, Cincinnati; Robert Cook, West Chester, all of Ohio

[73] Assignee: Ethicon, Inc., Somerville, N.J.

[21] Appl. No.: 917,636

[22] Filed: Jul. 20, 1992

Related U.S. Application Data

[63] Continuation-in-part of Ser. No. 779,436, Oct. 18, 1991, abandoned.

[51] Int. Cl.⁵ ............................................. A61B 17/072
[52] U.S. Cl. ..................................... 227/178; 227/19; 227/180
[58] Field of Search ................ 227/19, 180, 176, 178

[56] References Cited

U.S. PATENT DOCUMENTS

| | | | |
|---|---|---|---|
| 4,754,909 | 7/1988 | Barker et al. | 227/19 |
| 4,784,137 | 11/1988 | Kulik et al. | 227/19 X |
| 4,892,244 | 1/1990 | Fox et al. | 227/19 X |
| 4,955,959 | 9/1990 | Tompkins et al. | 227/180 X |
| 5,040,715 | 8/1991 | Green et al. | 227/8 X |
| 5,071,052 | 12/1991 | Rodak | 227/19 X |
| 5,170,925 | 12/1992 | Madden | 227/19 X |

*Primary Examiner*—Rinaldi Rada
*Attorney, Agent, or Firm*—Paul A. Coletti

[57] ABSTRACT

A stapler mechanism is described which contains a stapling assembly, and anvil assembly, firing means and knife means. These means are activated by a firing trigger. The anvil assembly is closed upon the stapling assembly by means of a closure trigger. The firing trigger is inoperable until the closure trigger has been activated. Another mechanism in the stapler is capable of locking the closure trigger after use so it does not spring open inadvertently before use of the firing trigger. Additionally, the stapler mechanism allows forward motion of both triggers and also is capable of allowing reverse motion of the closure trigger to open the mechanism.

22 Claims, 18 Drawing Sheets

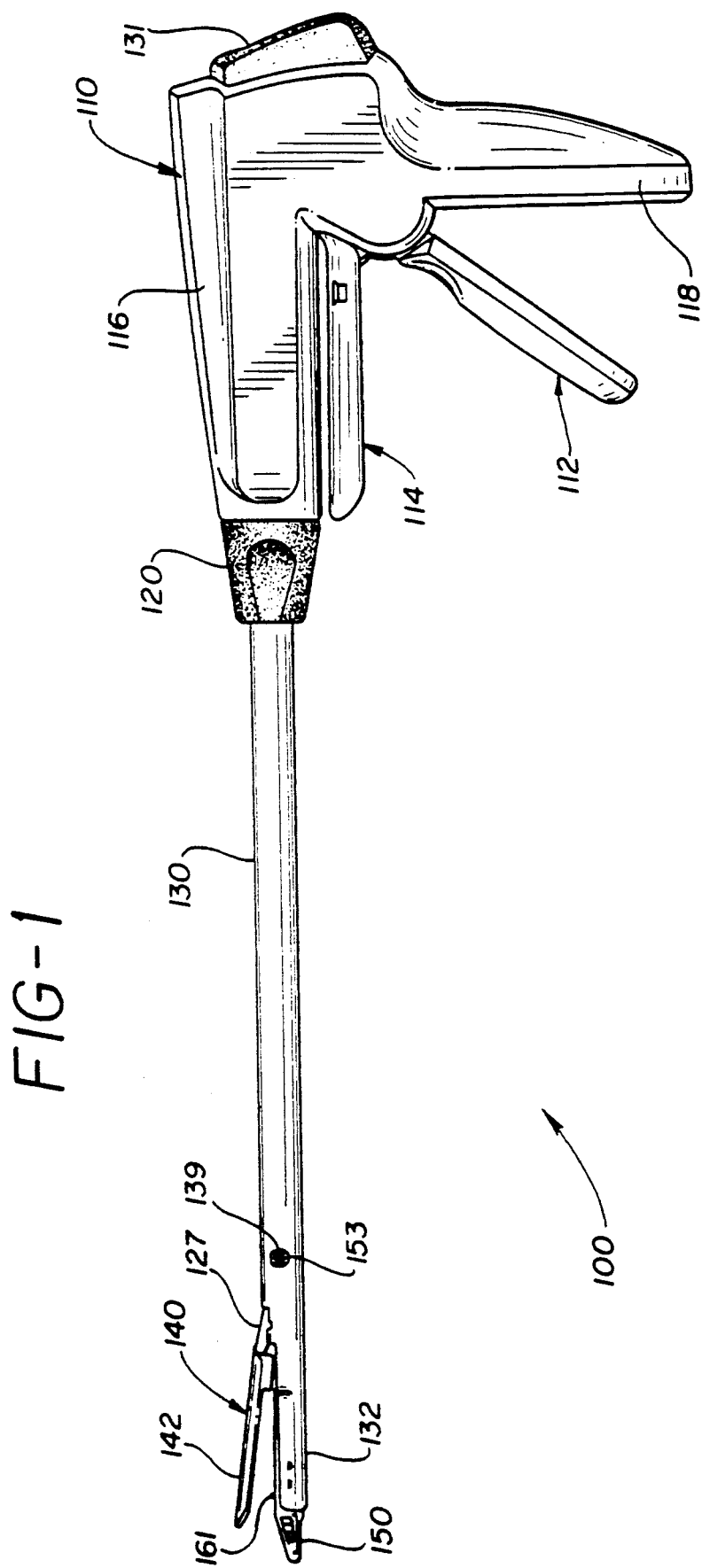

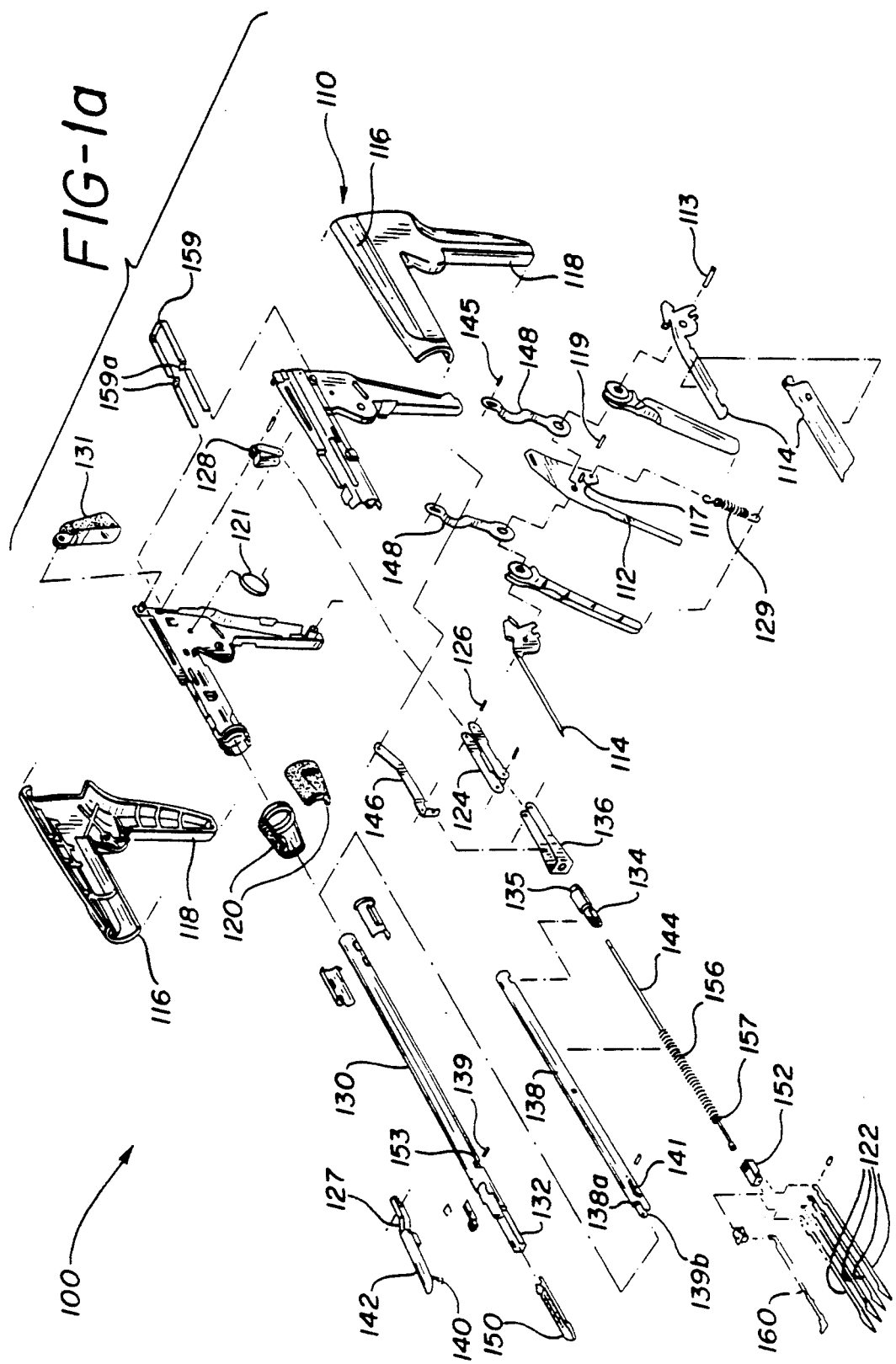

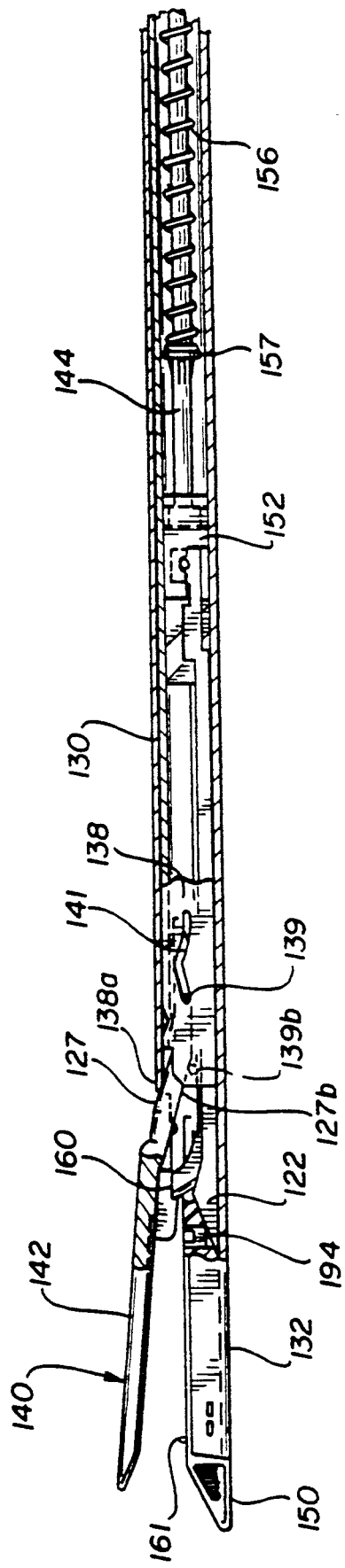

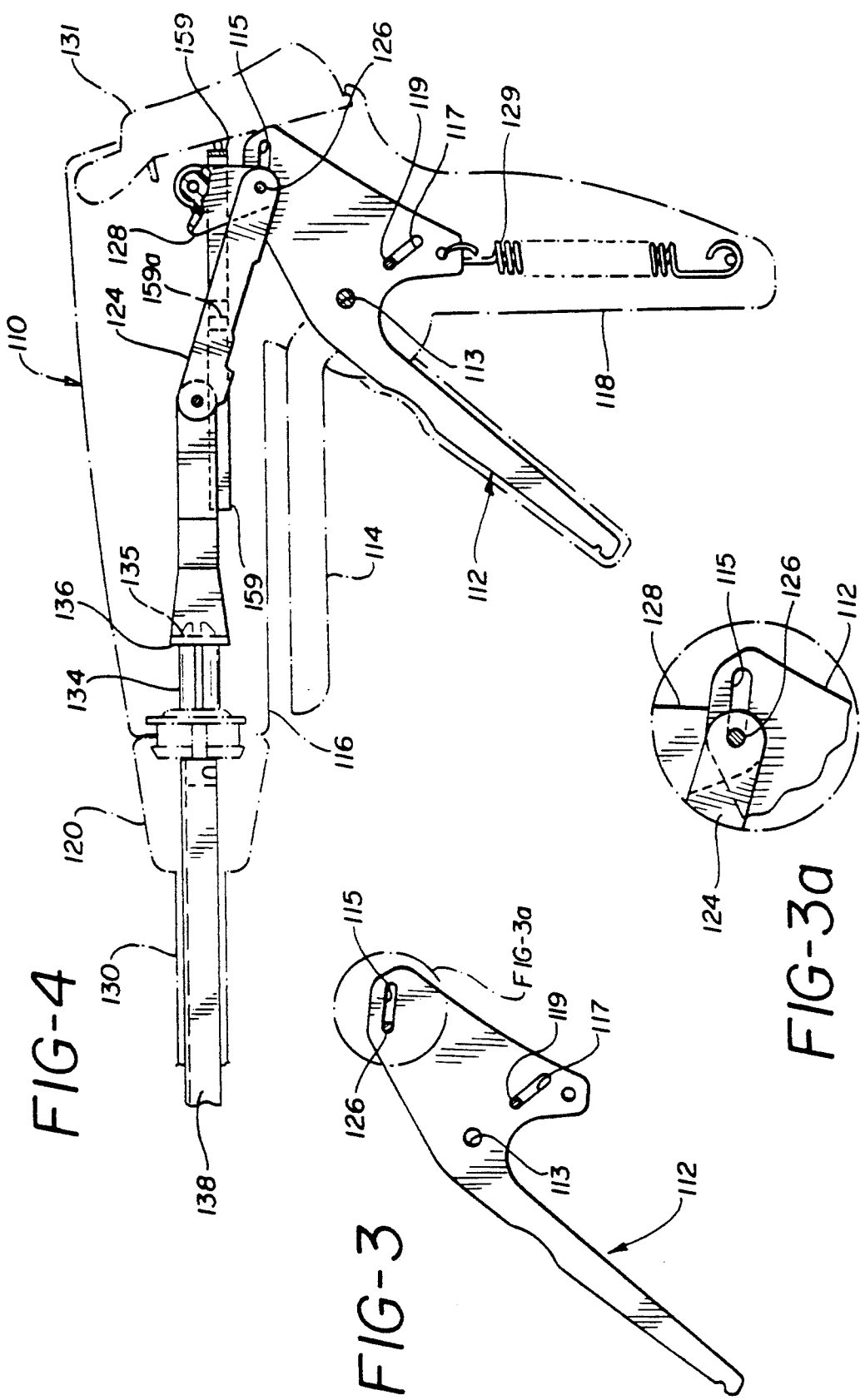

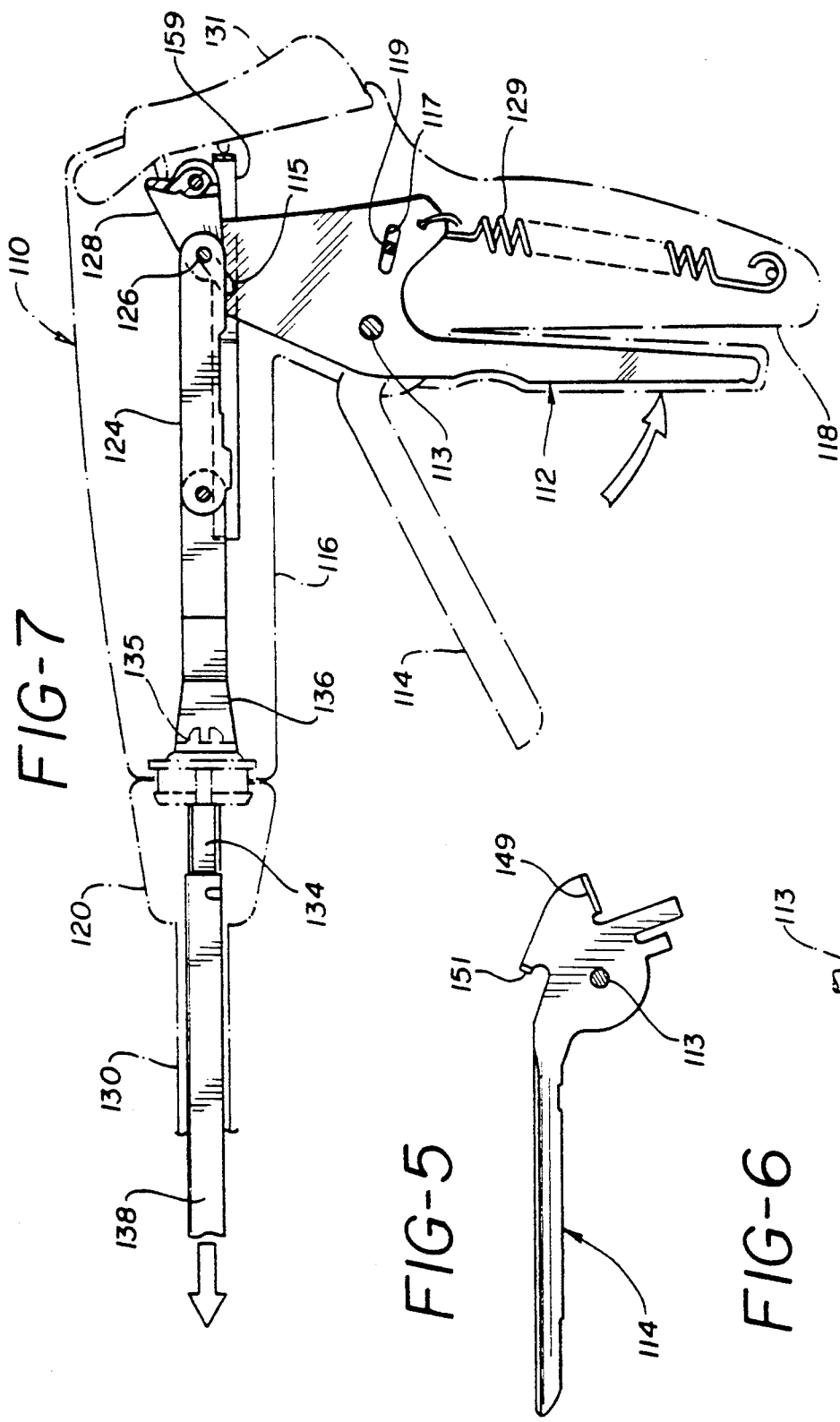

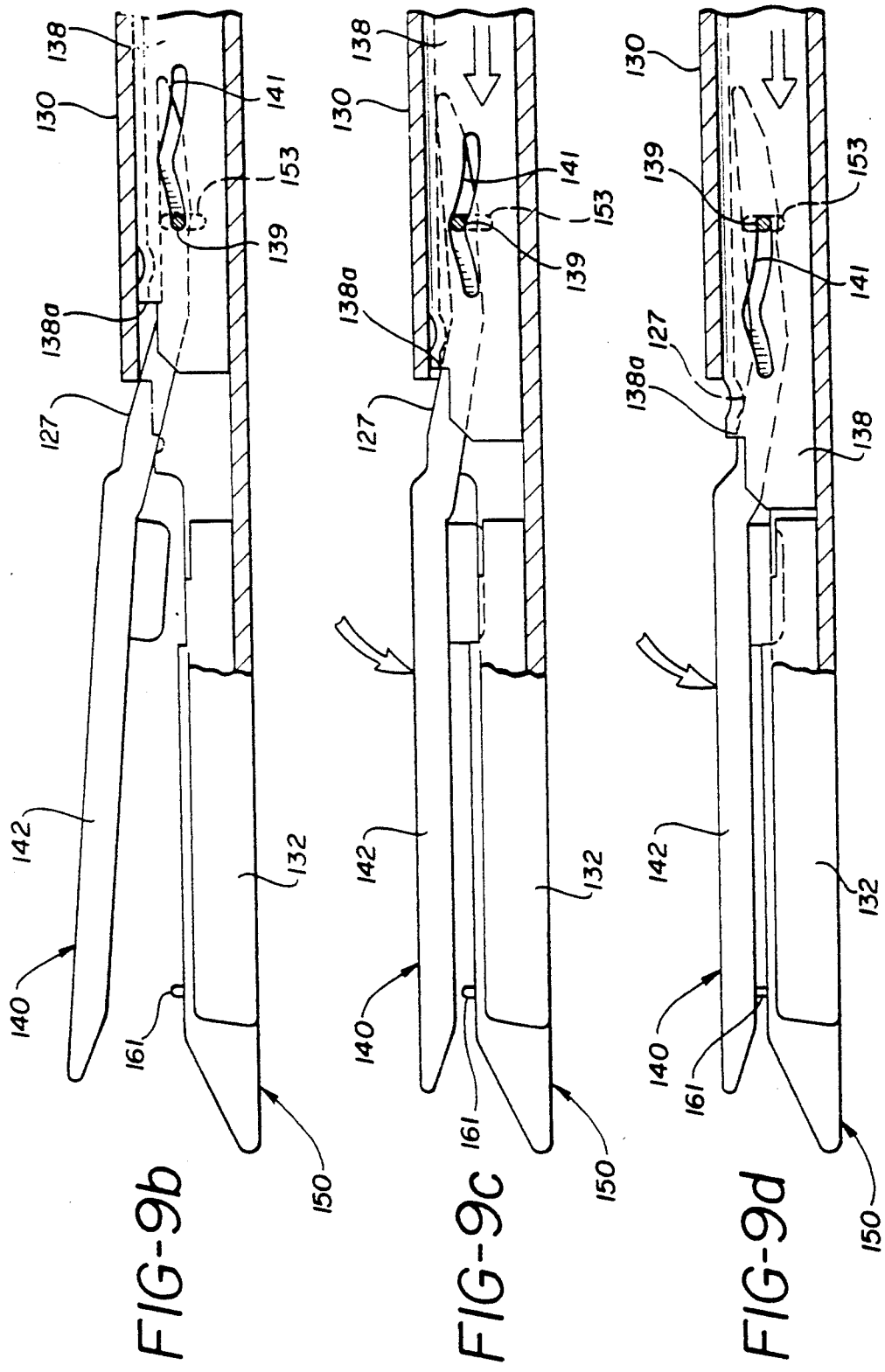

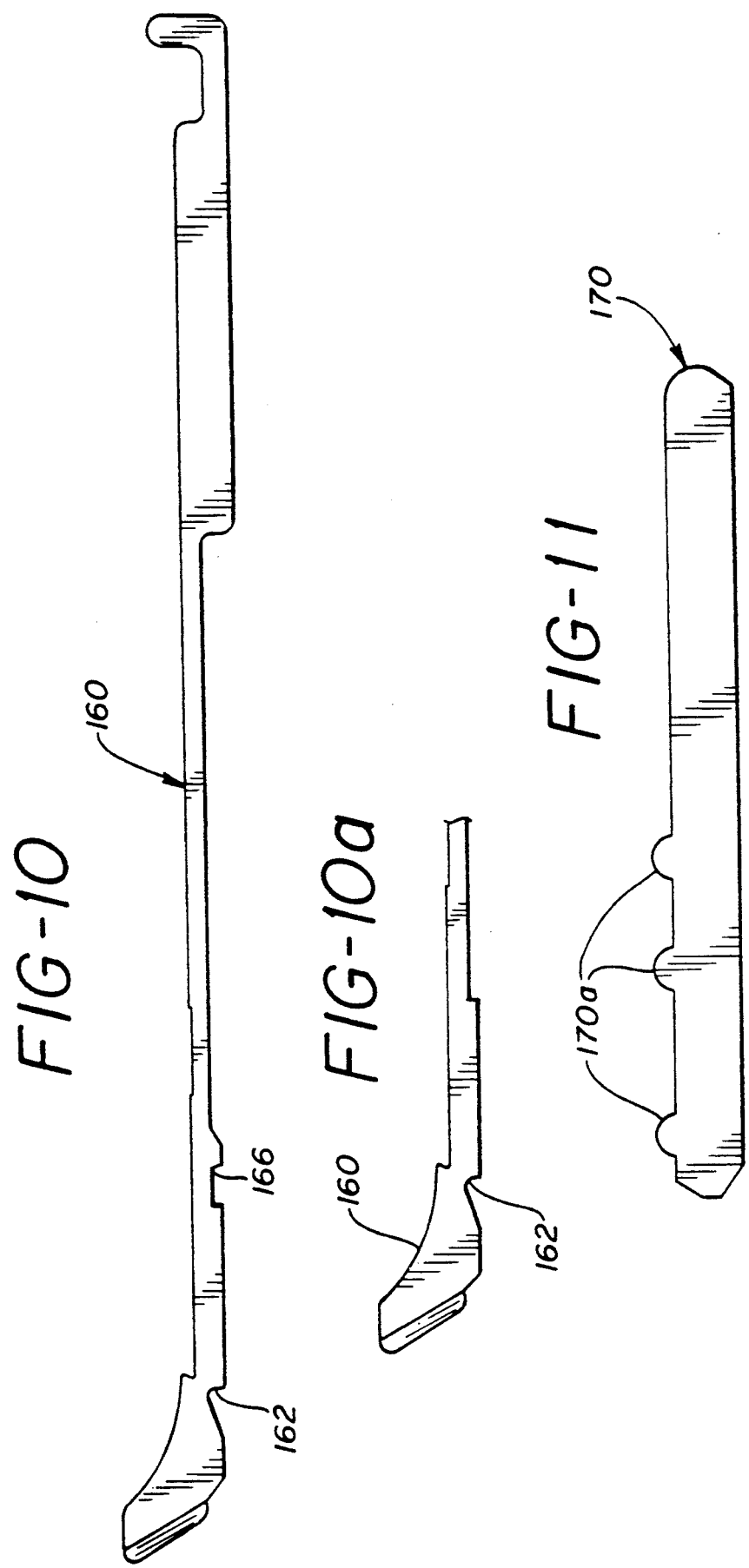

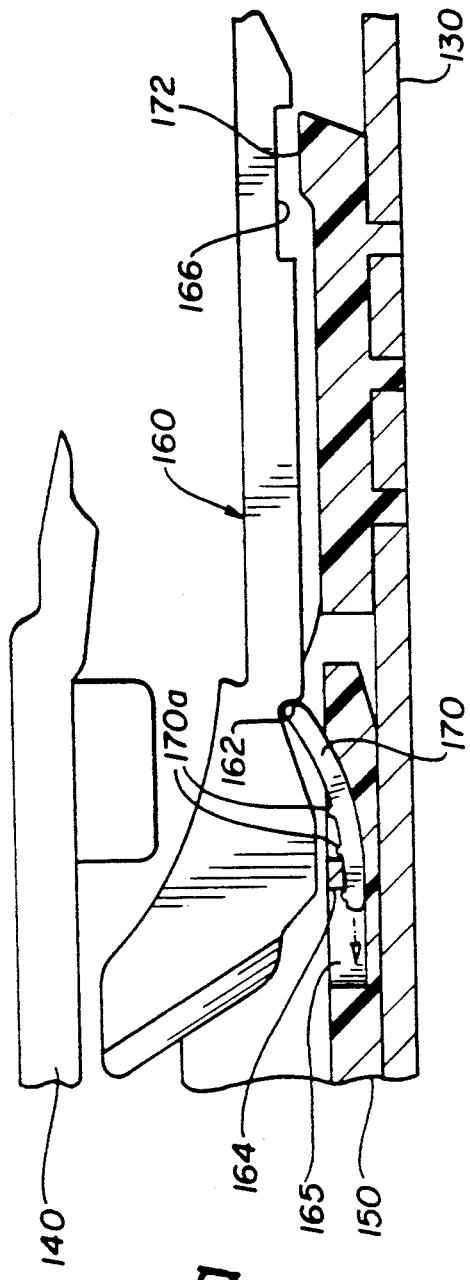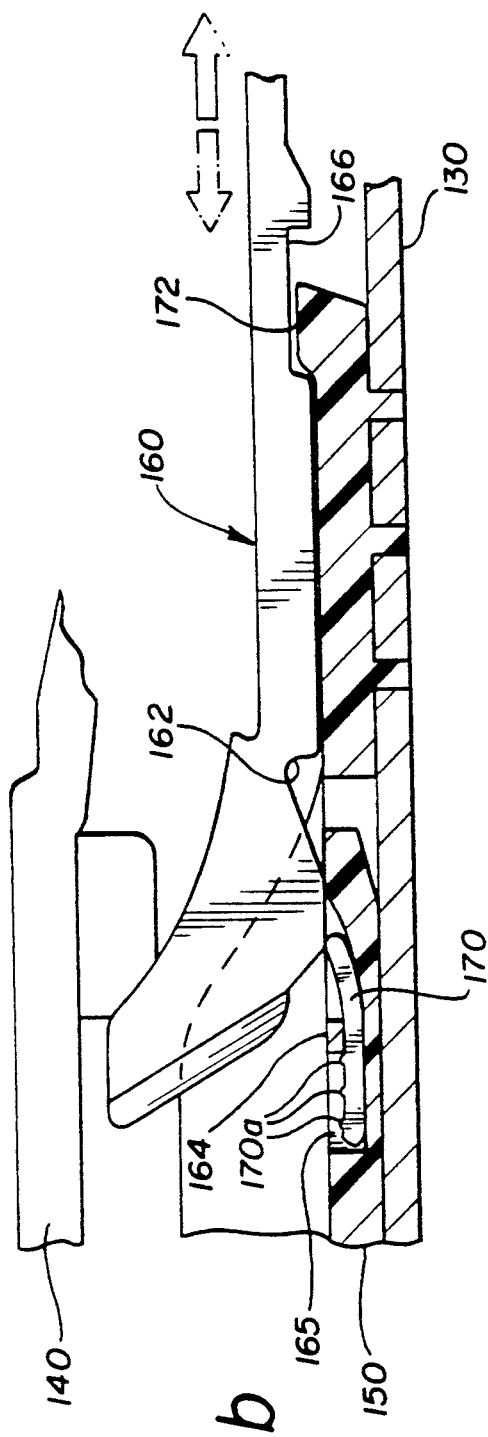
FIG-11a
FIG-11b

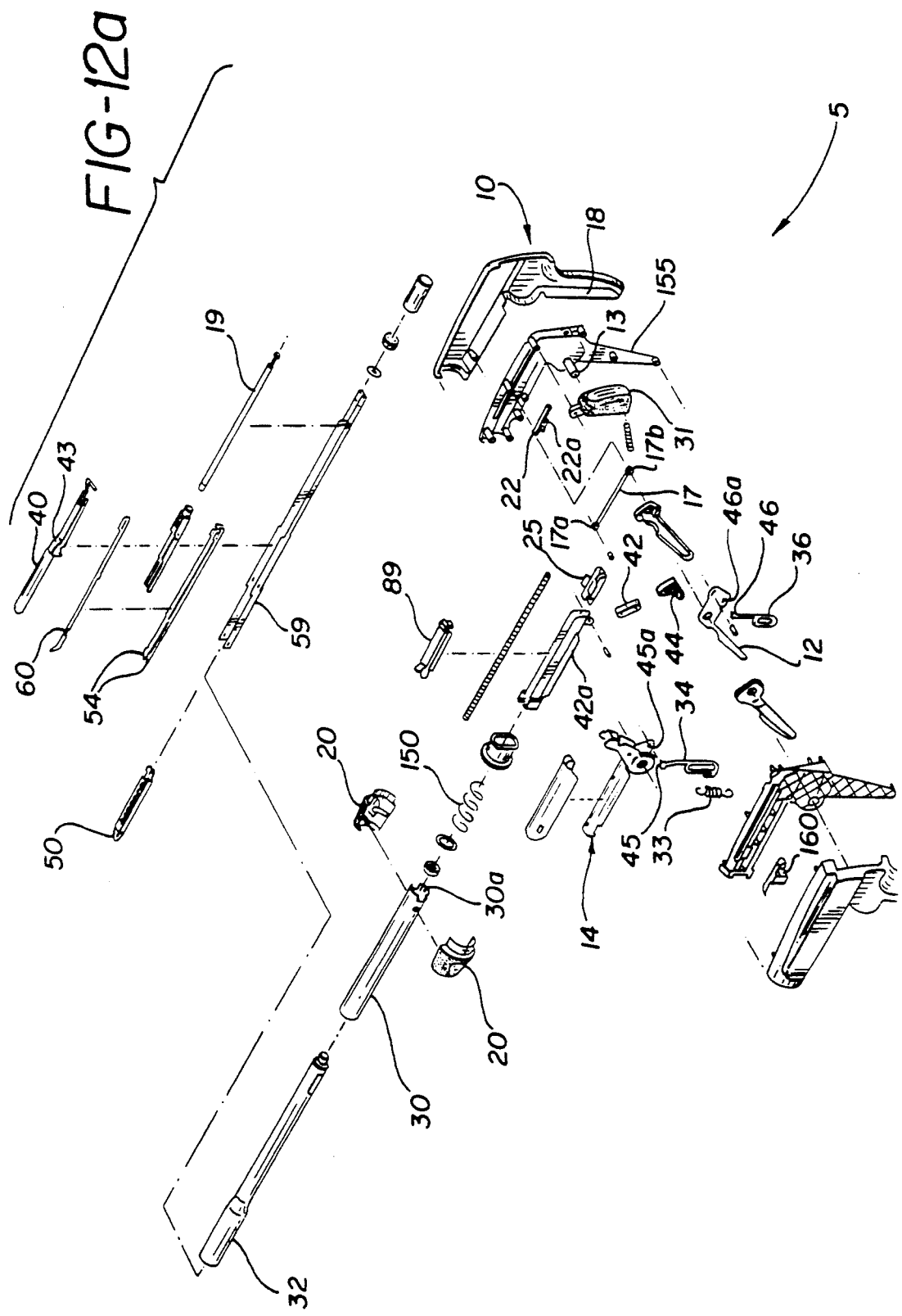

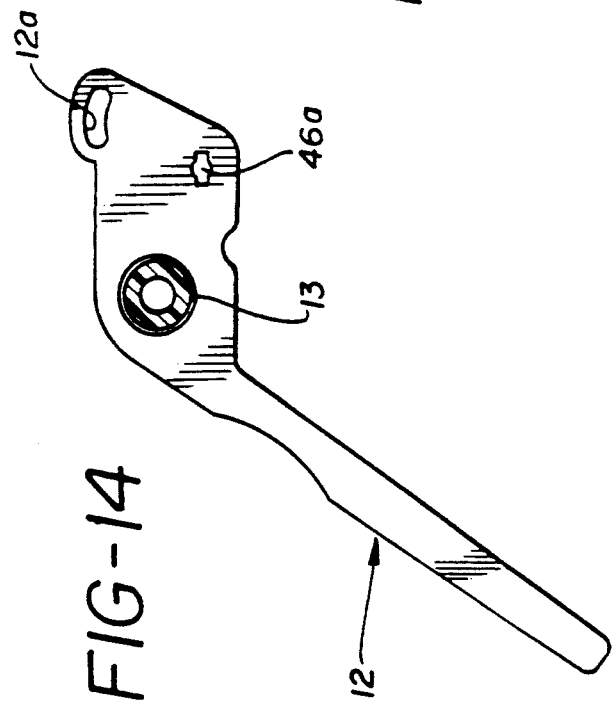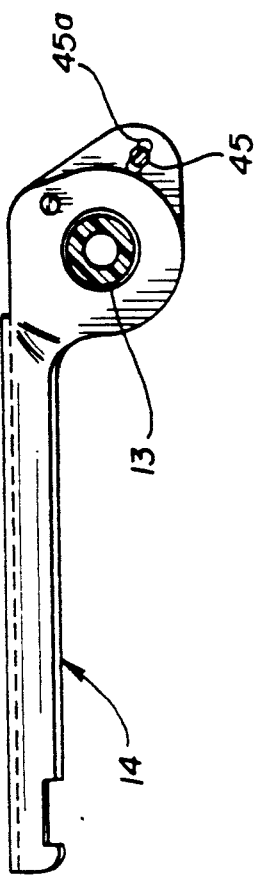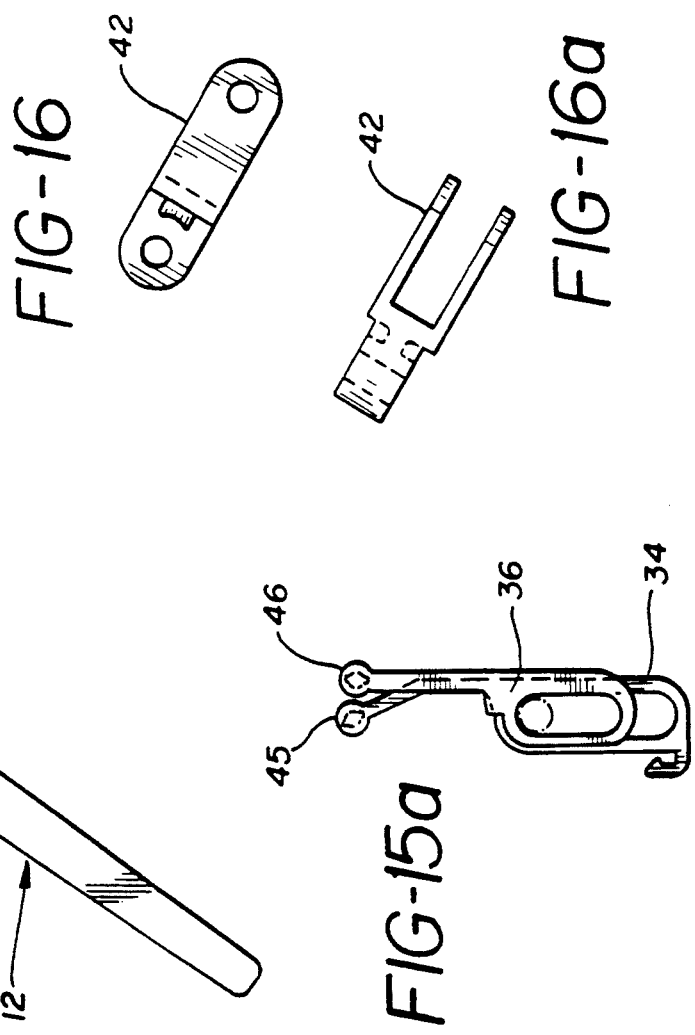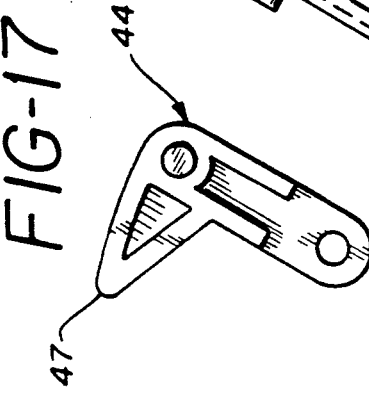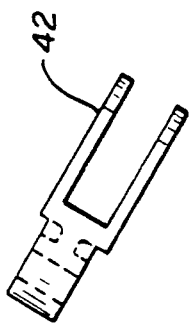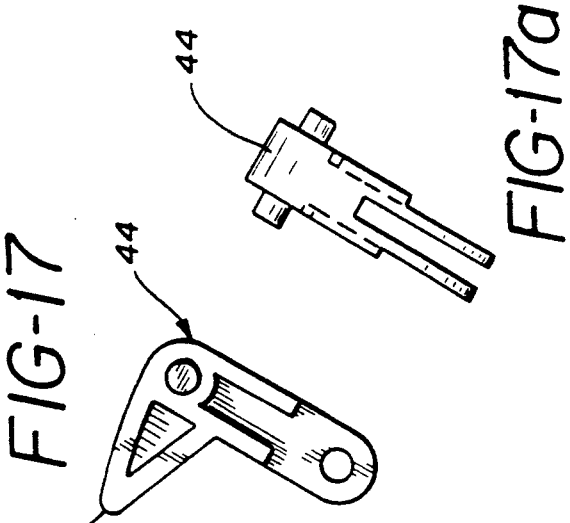

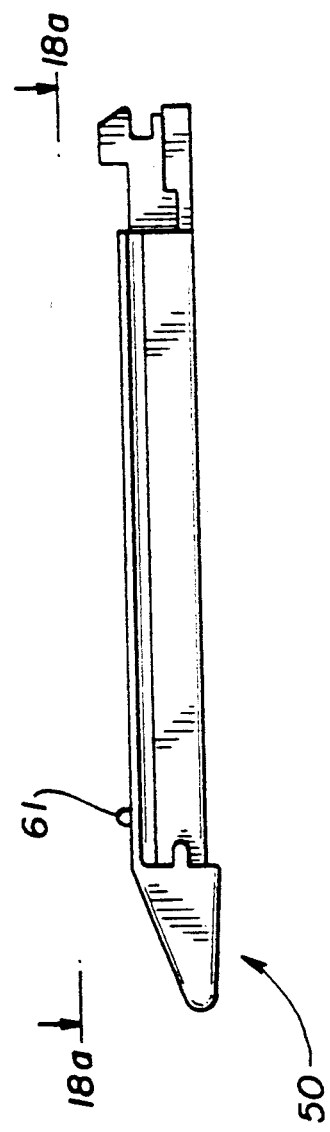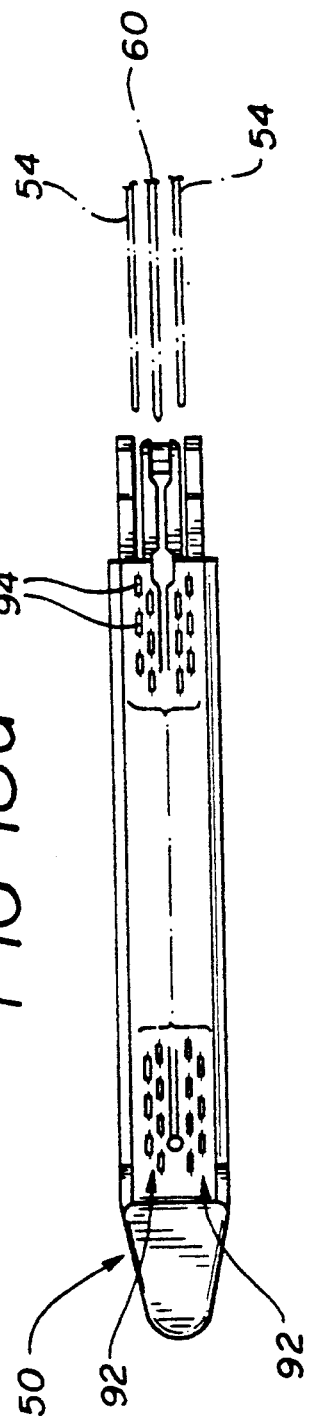

LINEAR STAPLING MECHANISM WITH CUTTING MEANS

This is a continuation in part of application Ser. No. 07/779,436 filed Oct. 18, 1991 now abandoned.

FIELD OF THE INVENTION

This invention relates generally to medical engineering, and more specifically it relates to laparoscopic or endoscopic surgery. Most specifically, it relates to a surgical stapling instrument which is capable of performing closures and cutting of lumen and tissue. This is accomplished in a mechanism which can be used endoscopically, that is through a trocar cannula or alone, through an incision, to both staple and cut tissue.

BACKGROUND OF THE INVENTION

In recent years surgery has markedly advanced through the performance of laparoscopic and endoscopic surgical procedures such as cholecystectomies, gastrostomies, appendectomies, and hernia repair. Also, the application of endoscopic surgical stapling and suturing instruments has been provided in cardiovascular and pulmonary surgery, as well as operative inventions in the gastrointestinal tract. Such endoscopic instruments are capable of providing hemostasis and also of cutting tissue. This reduces operating and recuperation time.

These stapling procedures are accomplished through a trocar assembly, which is a surgical instrument used to puncture a body cavity. The trocar contains a sharpened obturator tip and a trocar tube or cannula. The trocar cannula is inserted into the skin to access the body cavity, by using the obturator tip to penetrate the skin. After penetration, the obturator is removed and the trocar cannula remains in the body. It is through this cannula that surgical instruments are placed. Specifically, it is through this trocar cannula that surgical stapling instruments with cutting mechanisms are placed. One such trocar is the Endo-path ®trocar manufactured by ETHICON ENDO-SURGERY, Cincinnati, Ohio.

Nonetheless, certain deficiencies in current concepts for endosurgical stapling mechanisms have been recognized. One of the more important deficiencies is the fact that current stapling mechanisms can not cause clamping of tissue and firing of the stapler, including the knife mechanism, with the same position of the hand for the forward stroke of an actuator, such as a trigger. Thus, the user must aim the clamping mechanism to encapture the desirable tissue with one hand, and then, while making a forward trigger stroke with the opposite hand, cause the tissue to be stapled and cut. If the stapling mechanism provides a ratchet member for the actuator, this deficiency is really not overcome, for in such a mechanism there still must occur simultaneous clamping and stapling of the tissue. Then, if it is undesirable to staple the tissue in that location, the trigger must be fully reversed. This may result in inadvertent jamming of the system, and in some staplers this alternative is simply not capable of being performed.

Another perceived deficiency is that no current stapling mechanisms have a safety device in place which prevents firing of the stapler before tissue has been clamped. Typically, the stapling mechanism may begin to clamp tissue between an anvil jaw and a stapling jaw. However, in some instances, there will be firing of the stapling mechanism before the tissue is entirely clamped. The user may have the mechanism partially attached to tissue via partially expelled staples before the user has ascertained a desirable location of the stapler. In this way, once again, there is a certain amount of instability or uncertainty in applying such a device.

A design criteria in creating a system containing two separate mechanisms for clamping and firing tissue is the limitation of the human hand. Therefore, it is difficult to properly and conveniently position a pair of triggers or a pushbutton mechanism coupled with a trigger mechanism. Thus, there has been little focus or incentive to create stapling mechanisms whereby the user is capable of operating a stapler with two strokes, unless both can be accomplished in a one-handed operation without moving that hand from the handle of the instrument.

Naturally, it would be desirable to be able to perform these functions in a fully rotational system. This simply allows the user to obtain virtually any angle of approach to the surgical site without having to contort the arm or wrist in order to adequately approach the subject.

Also, there have been no mechanisms which provide opening and closure of a clamping mechanism occurring during reciprocating motion of a clamping trigger. What is desired would be to be able to forwardly or reversedly move a trigger and thereby obtain closure or opening.

Finally, it would also be desirable to have distal contact of the stapling jaws, and then proximal clamping. In this way, once distal contact is effectuated, the surgeon realizes and can actually visualize the amount of tissue clamped between the jaws. By distal contact is meant that the distal or far end of the anvil seats first on the gap spacing pin or cartridge. Without such distal contact, the surgeon may still be uncertain about the amount of tissue clamped, and therefore the firing force necessary to fire the mechanism.

SUMMARY OF THE INVENTION

It is an object of the invention to provide a stapling mechanism which is able to be used endoscopically, and may also be used in non-endoscopic procedures, and provides both stapling and cutting to the surgical site. It is desired to have tissue clamped between the jaws of the stapling mechanism, and it is also desired that the stapling mechanism accomplish this clamping and then firing in a two-part, sequenced operation.

It is further an object of the invention to provide a stapling and clamping mechanism whereby the clamping mechanism causes the stapling mechanism to be put into position for firing.

This novel concept also necessarily requires that one is prevented from actuating the firing mechanism before clamping is accomplished. Therefore, it is further an object of the invention to prevent firing of the stapling mechanism before the entire clamping procedure is completed or if a cartridge is missing or has been previously fired.

It is further an object of the invention to provide a rotational mechanism which accommodates stapling and cutting endoscopically.

It is further an object of the invention to provide a closure mechanism so that the closure mechanism is not able to inadvertently spring open before the firing mechanism has been fully actuated. It is yet another object of the invention to provide a mechanism which allows forward and reverse motion of a clamping trigger such that forward motion causes clamping, and then permits stapling, and reverse motion permits the jaws of the mechanism to be opened, by reversing the functions of the clamping mechanism.

Finally, it is an object of the invention to provide a closure mechanism in a surgical stapler which accomplishes clamping of the tissue to be stapled in a direction opposite that of stapling, that is, from the distal toward the proximal end of the stapler. In this way, proper amounts of tissue may be adequately clamped, and then stapled.

These and other objects of the invention are described in an endoscopic stapling mechanism which is capable of clamping, stapling and cutting tissue. The stapling mechanism utilizes a surgical stapling cartridge which contains at least two double rows of staples. The stapling cartridge also provides for knife means to divide the two double rows of staples during the stapling function. The stapling mechanism contains a unique trigger mechanism which contains a double trigger feature. One of the triggers causes clamping of tissue. The other trigger causes firing of the staples and actuation of the knife. Thus, clamping and firing are accomplished separately. Because the system contains a unique safety mechanism, there cannot be firing of staples before there is full clamping of tissue. In this mechanism, stapling is accomplished in any rotatable position, as soon as tissue has been clamped. Yet, the clamping trigger locks in position so that it will not inadvertently spring open during use of the firing trigger.

Uniquely, in one of the embodiments described herein, there is contained in the endoscopic stapling mechanism a double clutch mechanism which allows the user to derive benefits from both forward and reverse motion of the clamping and firing triggers. During forward motion of the triggers, there is clamping and then firing. During reverse motion, there is the capability of overriding any jams encountered by the stapling mechanism, and then allowing the stapled tissue to be removed from the stapling site.

Finally, in this invention there is the capability of having distal clamping of tissue, even larger tissue held within a larger size device. After this clamping, there is then proximal contact of the stapling and closure means and thereafter, similar proximal contact of the knife mechanism. Thus, while it is easily ascertainable how much tissue is clamped between the clamping mechanisms, it is also easy to determine whether clamping and stapling have been properly accomplished.

These and other objects of the invention will be better understood from the following attached Detailed Description of the Drawings, when taken in conjunction with the Detailed Description of the Invention.

DETAILED DESCRIPTION OF THE DRAWINGS

FIG. 1 is a side elevational view of an endoscopic linear stapling and cutting mechanism of the present invention;

FIG. 1a is an exploded perspective view of the instrument of FIG. 1;

FIGS. 2a and 2b are cross-sectional views of the view of FIG. 1;

FIGS. 3 and 3a are individual and closeup views of the closure trigger of the present invention;

FIGS. 4 and 7 are operational views of the closure trigger and toggle linkage of the invention;

FIGS. 5 and 6 are isolated side and top views of the firing trigger of the invention;

FIGS. 9b, 9c and 9d are side operational views of the interaction between the stapler shaft, the cartridge, and the anvil closing mechanism;

FIG. 10 is a side isolated view of the knife means with a lockout notch;

FIG. 10a is a side view of an alternate knife means with no lockout notch;

FIG. 11 is a side isolated view of the lockout member contained in the cartridge of FIGS. 8 and 8a.

FIGS. 11a and 11b show the motion of the lockout member of FIG. 11 when moved by the knife means of FIG. 10 in the cartridge of FIG. 8;

FIG. 12a is an exploded perspective view of the instrument of FIG. 12

FIG. 14 is a side view of the closing trigger plate of the embodiment as described in FIGS. 12 and 13;

FIG. 15 is a side view of the firing trigger as seen in FIG. 13 of the present invention;

FIG. 15a is a side view of the trigger return linkage of the alternate embodiment of this invention;

FIGS. 16 and 16a are isolated views of the front toggle link as seen in FIG. 13 of the present invention;

FIGS. 17 and 17a are isolated plan views of the rear toggle link as also described in FIG. 13 of the present invention;

FIGS. 18 and 18a are isolated side and top views of another typical cartridge, as used in the stapler of FIG. 12;

Figure 12:
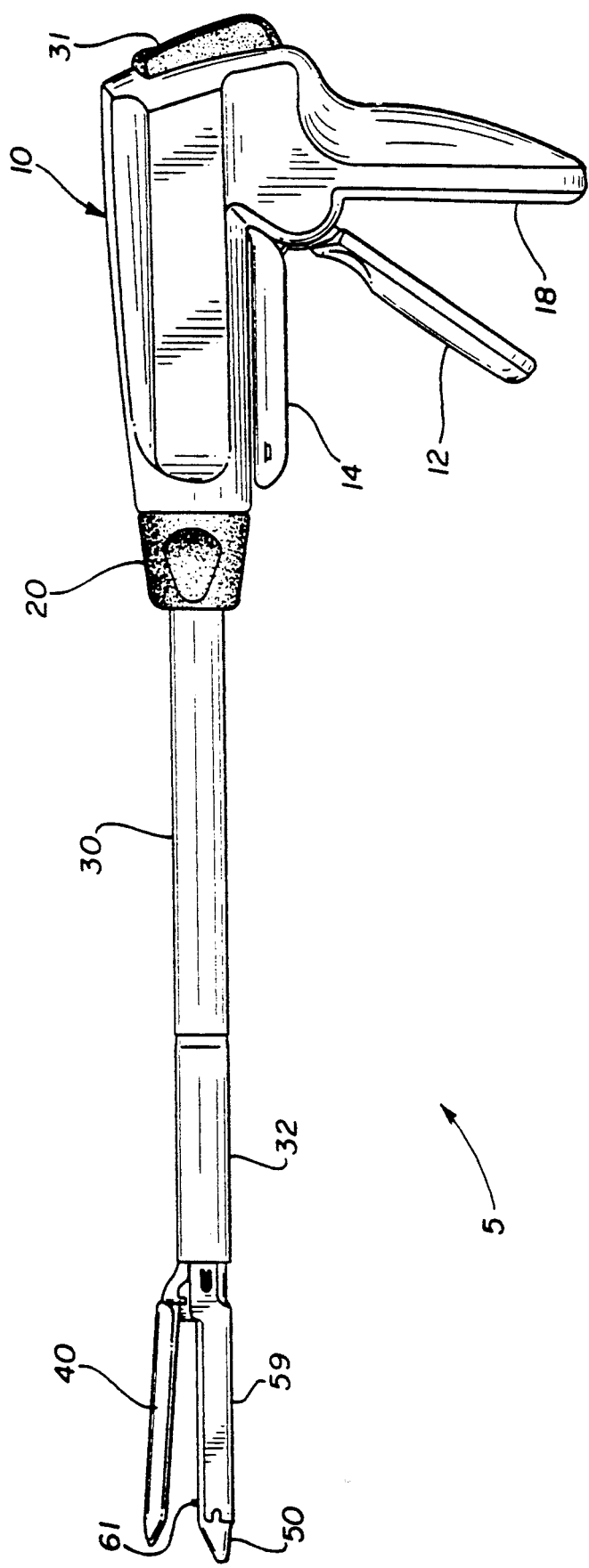
FIG. 12 is a side elevational view of an alternate preferred embodiment of the stapler of the present invention.
Figure 13:
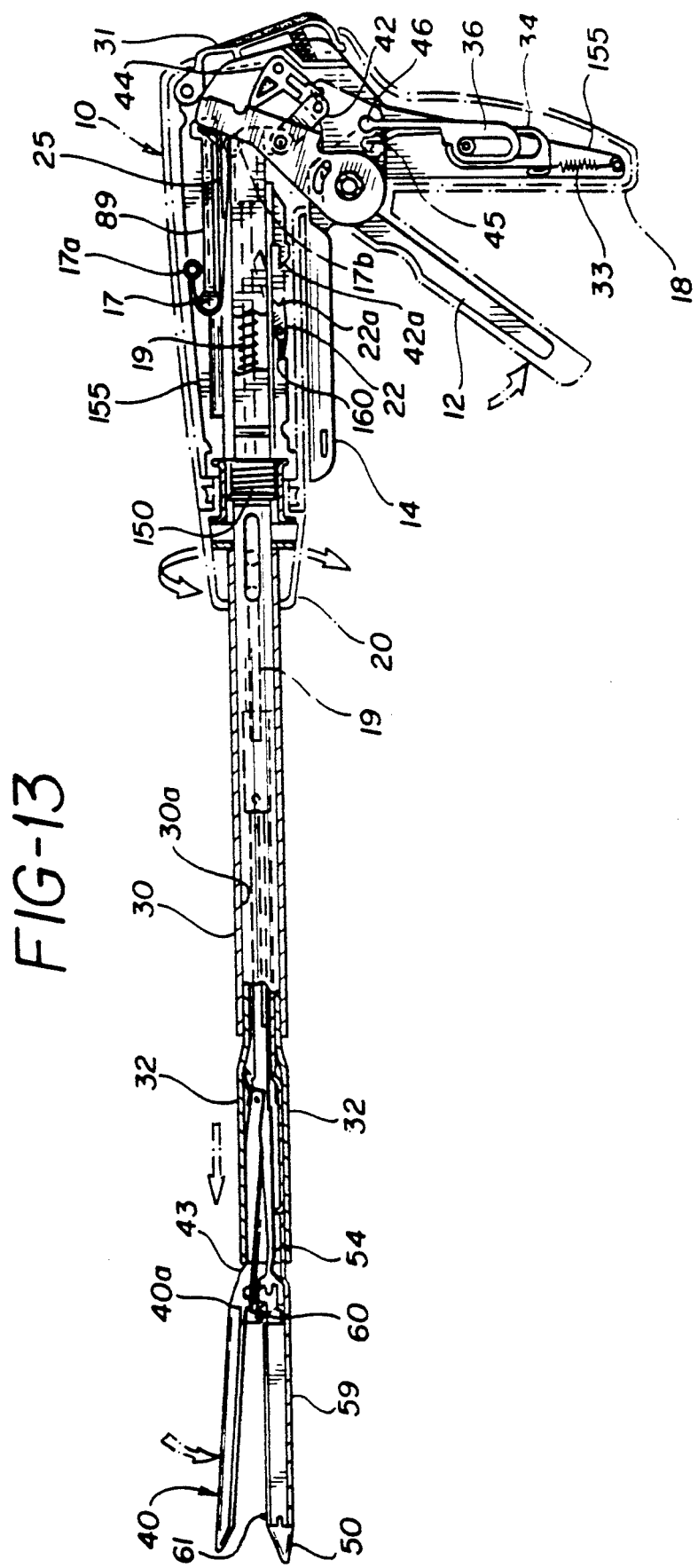
FIG. 13 is a cross-sectional view of the stapler of FIG. 12.
Figure 19:
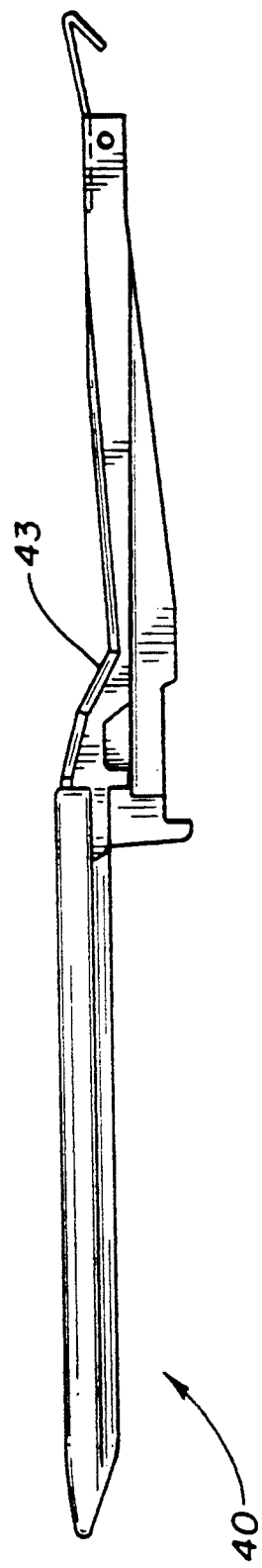
FIGS. 19 and 19a are isolated side and bottom views of the anvil member used in the stapler of FIG. 12.
Figure 19A:
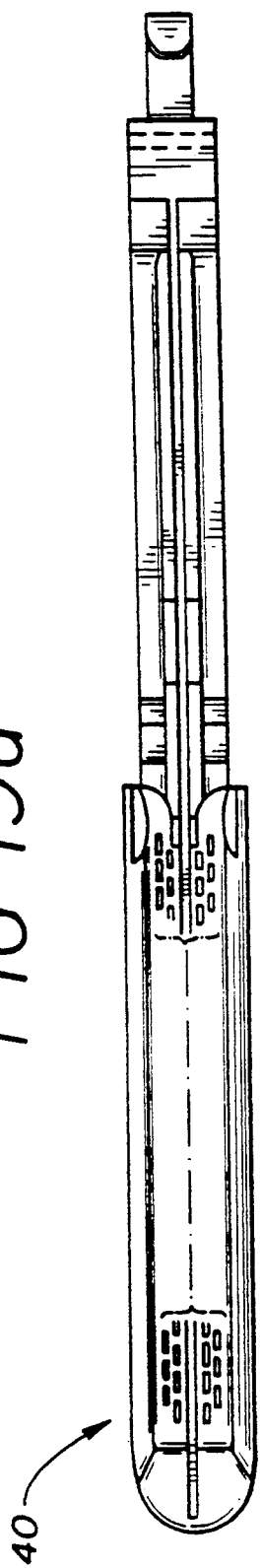
Figure 20:
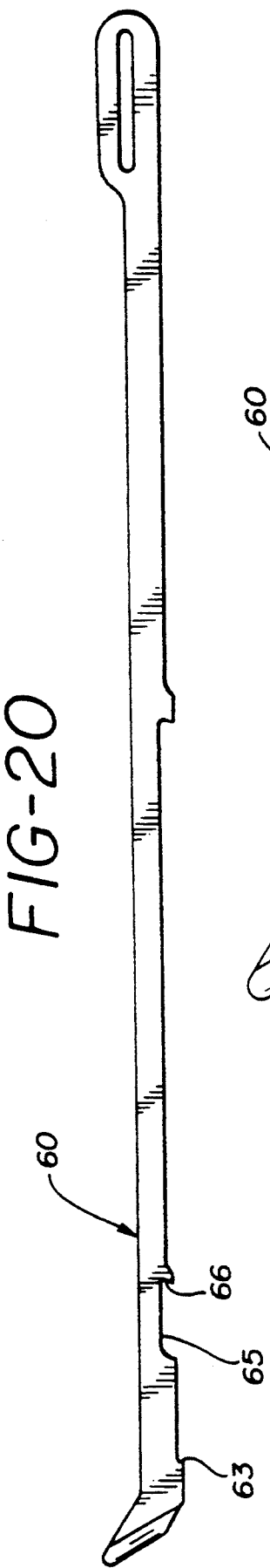
Figure 20A:
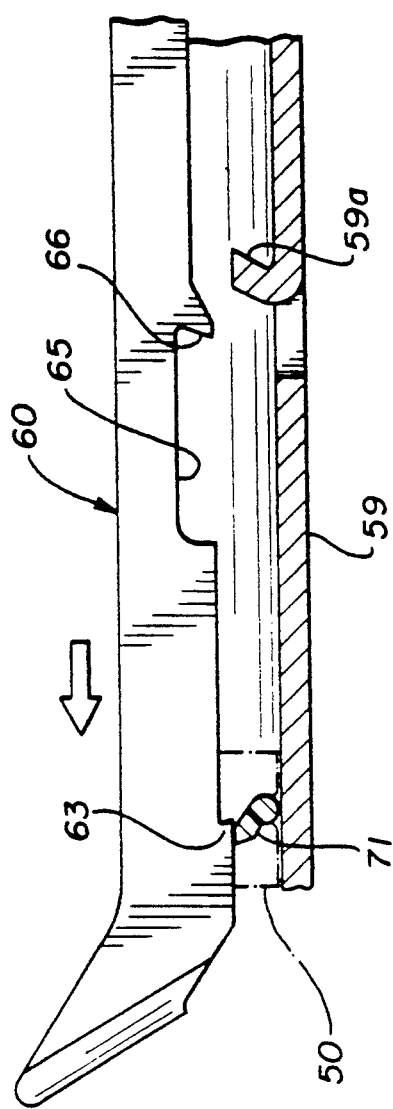
Figure 20B:
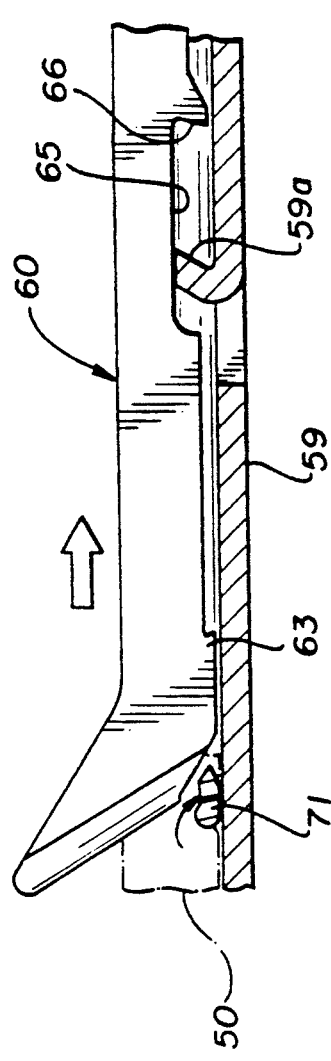

FIG. 20 is a detailed view of the knife mechanism and lockout notch as used in the cartridge of FIG. 18, as seen in the views of FIGS. 12 and 13 describing the alternate embodiment of the present invention; and FIGS. 20a and 20b are views of the lockout mechanism before and after motion of the knife means of FIGS. 19 as in the stapler of FIGS. 12 and 13.

DETAILED DESCRIPTION OF THE INVENTION

As can be seen from FIGS. 1, 1a, and 2, in one embodiment of the surgical stapler of this invention, there is described a stapler 100 which contains a handle portion 110, rotating means 120, a shaft portion 130, anvil portion 140, and cartridge assembly 150. A knife means 160 is slidable within the cartridge assembly 150 to cut tissue. In the handle portion 110 there is a first or closure trigger (also called a clamping trigger) 112, and second or firing trigger 114. The clamping trigger 112 causes the anvil portion 140 to come into proximity of the cartridge assembly 150. The firing trigger 114 causes the wedges 122 located in the shaft 130 to move through the cartridge assembly 150, and also causes the knife means 160, also located in the shaft 130 to move through the cartridge assembly 150, in order to cut tissue.

As can be seen in more detail in FIGS. 1a, 2a, 2b, 3, 4, 5, 6 and 7 the endoscopic linear stapling mechanism 100 contains a double trigger mechanism. The first or clamping trigger 112 is for closing the jaws 132, 142 of the instrument onto tissue, and the second or firing trigger 114 is used for firing the stapler 100. The intent of the double trigger design is to combine one-handed use within a stapling mechanism, and to make such one-handed use so that it is impossible to form staples unless the instrument is fully closed.

When the instrument is initially loaded, with cartridge assembly 150 held within shaft portion 130 on jaw 132, the firing trigger 114 is flush with the body 116 of the instrument, so that it is parallel with the shaft portion 130, and is for all practical purposes inaccessible to the user. During actuation of the clamping trigger 112, the firing trigger 114 swings into a "ready" position preparatory to actuation. This position is 35° to 45° spaced apart from the closure trigger 112, which has now moved into position against base 118. As will be later described, a multiplier mechanism causes the firing trigger 114 to move through a greater arc than closure trigger 112.

The closure trigger is spring-loaded, so that an incomplete closure results in the closure trigger swinging open to its position as seen in FIGS. 1 and 2, once again spacing the firing trigger 114 away from the reach of the hand operating the mechanism. A closure sequence must therefore be completed, with the clamping trigger 112 locking proximal to the base 118, before the firing trigger 114 can be grasped or is operational by the user.

As can be seen from the FIGS. 1a, 2, 3, 3a, 4 and 7, the closure trigger 112 is attached to a front closure link 124. at pivot pin 126. Closure trigger 112 is also attached to a rear closure link 128 which pivots inside the handle 110 of the stapler 100. The closure trigger 112 therefore is capable of pivoting around the handle portion at pivot 113, so that it moves roughly 25°-50°, in this instance, preferably 35°. The closure trigger 112 is spring-loaded at spring 129 so that unless the closure trigger 112 is fully rotated toward the base 118, the spring 129 causes the closure trigger 112 to reopen to its initial position. As will be later explained, it is the motion of this closure trigger 112 which causes the anvil portion 140 to clamp into proximity of cartridge assembly 150.

Furthermore, the closure trigger 112 is connected by means of a pin to the firing trigger 114. Thus, as can be best seen in FIGS. 2b, 3, 5 and 6, the closure trigger 112 is linked with the firing trigger 114 by means of a pin 119 which moves in a guided path along slot 117 away from the axis of rotation of the closure trigger 112. This pin 119, in turn, moves along a path within slot 117 of the firing trigger 114. As better seen in FIGS. 2b, 5, 6 and 7, the rotation of the closure trigger for approximately 35° results in rotation of the firing trigger for approximately 45°. The control of the pin 119 is accomplished by guide plates placed in the body 116 of handle portion 110. Now, closure trigger 112 is in place at the base 118 of handle 116. Firing trigger 114 needs to travel only 30°-60° to complete a full firing stroke. This arc is quite manageable for even the smallest human hands.

After its initial rotation, this guiding pin 119 no longer acts upon the firing trigger 114. That is, this guide pin 119 is no longer in contact with the firing trigger 114. This allows the firing trigger 114 to complete its rotation and fire staples without interaction of guide pin 119 or with the closure trigger 112. Thereby, the firing trigger 114 is connected to a spring 121 as seen in FIG. 1, which is in turn connected to the handle 110. This spring causes the firing trigger 114 to return to the 45° position so that triggers 112, 114 may be returned during opening of the instrument 100.

Figure 2B:
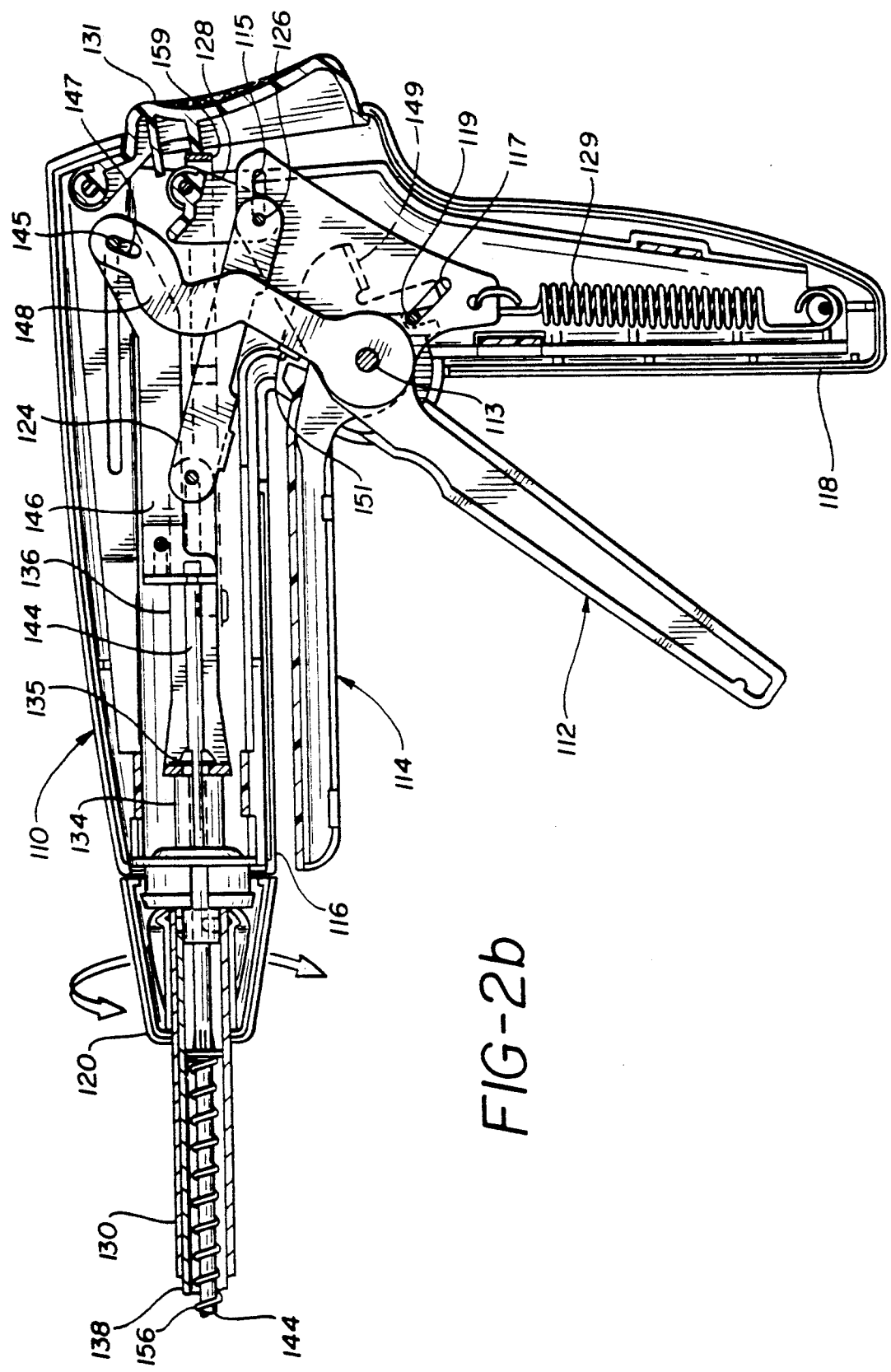

As can be seen in FIGS. 1, 1a and 2b, and especially in FIG. 4, there is contained a locking mechanism comprising button 131 which activates leaf spring involution 159a on leaf spring 159, in order to cause the closure trigger 112 to be locked once it reaches base 118 of the handle 116. The closure trigger 112 is locked in place by leaf spring 159 which seats under front closure link 124 thus immobilizing pin 126. This in turn restrains closure trigger 112. The safety button 131 is pivotally mounted to the proximal top of base 118 and rests upon leaf spring 159. As will later be explained, thereafter, the firing trigger 114 is free to move alone.

As further can be seen from FIG. 2b, 4 and 7, motion of closure trigger 112 causes motion of front and rear closure links 124, 128. These front and rear closure links 124, 128 cause motion in line with the shaft 130 of a closure sliding member 136. This closure sliding member 136 is attached in a rotatable fashion at joint 135. On the distal side of joint 135 is closure coupler 134, which attaches to the end of a closure channel 138. It is the closure channel 138 which is attached to the pin 139 in the shaft 130 that connects this mechanism to anvil 140.

Closure channel 138 causes closure of the anvil portion 140 into proximity and alignment with the cartridge assembly 150. This is accomplished in that the closure links 124, 128 first move parallel to the axis of the shaft 130, as in FIG. 7, from their original positions in FIG. 4. Closure channel 138 is caused to slide within shaft 130. The front top surface 138a of closure channel 138 pushes forward and down on the anvil. This causes anvil 140 to come parallel to cartridge assembly 150 so that there is alignment of cartridge 150 and anvil 140. The shaft 130 is formed from a stationary tube, so that the closure channel 138 moves within the shaft 130 at the distal end of the instrument 100.

This double trigger mechanism 112, 114 has the following advantages. The firing trigger 112 cannot be actuated until the closure trigger 114 has been completely snapped into its final position, due to locking of the closure trigger 112 inside the handle 110. Therefore, one is certain that tissue has been clamped before the firing trigger 114 has been placed into motion. The firing trigger 114 can be actuated without repositioning the hand following closure of the instrument. That is, the hand stays stationary, and is once again gripped around the firing trigger 114, with closure trigger 112 maintained at the base 118 of the handle 110. This facilitates rapid completion of the firing sequence without requiring the surgeon's attention on the stapler away from the endoscopic video screen and thereby away from the operating arena. In addition, both the closure trigger 112 and the firing trigger 114 utilize a mechanism which is familiar to those who use surgical instruments, a pistol grip with a trigger type actuation.

As has earlier been explained, the closure trigger 112 pushes on the central pivot pin 126 of a toggle linkage 124, 128. Central pivot pin 126 rides in slot 115. This central pivot pin 126 results in relatively large amounts of motion in the closure channel 138 (see FIG. 4) which results in gross closure of the instrument 100. The mechanical advantage provided by the toggle linkage 124, 128 during this portion of closure is relatively small.

This has the advantage of providing the user with high tactile feedback. That is, the user is readily able to tell whether the system is overloaded with tissue. Near the position wherein movement of the toggle linkage 124, 128, (FIG. 7) is nearly complete, the closure trigger 112 has moved into place at base 118, and front closure link 124 and rear closure link 128 have been made generally parallel to the shaft 130, relatively little motion of the linkage 124, 128 results from any given rotation of the trigger 112. Trigger 112 rotation at this point provides significantly higher closure force than during the first portion of its motion. This is critical in accomplishing preloading of anvil 140 during the final portion of closure, and is in theory only constrained by the structural limitations of the system, as well as the force able to be applied by the user.

As can be seen from FIGS. 2b, 5 and 6, firing is accomplished by a simple rotation of the firing trigger 114 acting as a lever arm about pivot 113. The firing trigger is linked to the firing or driver rod 144 and driver rod link 146 by means of firing links 148. These firing links are engaged with the firing triggers by means of a clutch. This clutch mechanism is better seen in the top view of the firing trigger as seen in FIG. 6. This clutch mechanism does not engage the firing link 148 until the firing trigger 114 is in a "ready to fire" position, whereby hook 149 engages link 148. This eliminates the potential for firing the instrument prior to complete closure of the mechanism by closure trigger 112.

Once the clutch system has engaged the firing link 148, this causes the driver rod link 146 to be translated by pin 145, and moving with link 148 in slot 147, in a generally parallel position to the shaft 130 of the mechanism. This driver rod link 146 is connected to driver rod 144 which is rotatably connected in nozzle 120 to a pusher block 152 contained in the shaft 130. This pusher block is connected to firing wedges 122 and knife mechanism 160, as seen at the proximal edge of the shaft 130 which enters the cartridge assembly 150. The firing wedges 122 are able to transversely move staples loaded in the cartridge assembly 150 so that they are fired into the anvil portion 140, as best seen in FIGS. 2a, 8, 8a, 9 and 9a, and as well known in the art. The knife mechanism 160 is capable of cutting tissue between the completed pair of double or triple rows(or more) of staples, as also is well known in the art.

After firing has been completed, the firing mechanism returns by means of a compression spring 156 placed about driver rod 144 along shaft 130, so that spring 156 is stationary at base 157, which causes the driver rod 144 to be moved in a direction reverse from firing. Spring 156 itself has a sufficient strength to also cause driver rod 144 to move the firing link 148 via linkage 146 to return to its ready to fire position. This similarly causes the driver rod 144 to pull the wedges 122 and the knife 160 so that they are removed from the cartridge assembly 150. If the wedges 122 or the knife 160 do not return, that is if they are jammed, the firing mechanism comprising the firing trigger 114 contains a reverse clutch assembly which allows the firing trigger 114 to engage with the firing link 148 at hook 151 (FIG. 6) so that it is capable of causing this assembly to move in a reverse or rearward direction. This provides a backup to the system, in the event there is a failure in the driver return spring 156 or if the instrument has inadvertently been misassembled.

The system also contains a safety mechanism which locks the closure trigger 112 in its closed position. This safety mechanism is a leaf spring 159 which interacts with the safety button 131 on the rear of the instrument. Side plates on the portion of the toggle linkage assembly 124, 126 cause the leaf spring to remain in a tensioned position, and guide the leaf spring during its motion. When the front closure link 124 is in its straightened position, so that the rear closure link 128 is also rotated to be generally parallel with the shaft 130, the leaf spring 159 has been tensioned to restrain the toggle linkage 124, 128 in its parallel position. The safety button 131 on the rear of the instrument thereafter urges the leaf spring 159 in a forward direction, toward the cutting mechanism. This forward motion of the spring 159 causes the toggle linkages 124, 128 to be freed from the restraint of the spring 159. This motion allows freedom of movement for closure trigger 112.

As has been previously described, and as better seen in FIGS. 2a, 8, 9 and 9a-9d, the jaws 132, 142 of this instrument are closed by means of a cam surface 127 on the outer surface of the anvil 140. The anvil 140 pivots about pin 139 embedded in slot 141 of the closure channel 138 in shaft 130. Channel 138 is pushed forward With the actuation of the closure trigger 112. Closure channel surface 138a bears upon the cam surface 127 of the anvil 140, forcing it to pivot and move transversely within slot 153 contained in shaft 130. The location of the slot 153 as compared to the surface profile of the cam 127 determines motion of the anvil 140, such that the slot 153 and slot 141 combination forms a "fixed" pivot, which is fixed only with respect to the anvil 140. Therefore, anvil 140 is allowed to move transversely across the axis of a stationary tube 130. Shaft or stationary tube 130 forms the "ground" position for the pivot pin 139, so that its motion is only transverse compared to the shaft 130.

As better seen in FIGS. 9b-9d, the motion of the anvil 140 follows a predetermined path. First, the anvil 140 is rotated to a position parallel to cartridge 150. Then, anvil 140 moves in a direction transverse to the axis of shaft 130, maintaining its parallel alignment with cartridge 150, until it is abutting pin 161 on cartridge 150.

This mechanism is also assisted by surface 127b on the opposite side of anvil 140. This is better seen in FIG. 9. This second cam surface 127b on the opposite portion of the proximal end of anvil 140 rides on buttons 139b held within the closure channel 138 during opening of the instrument. Second cam surface 127b similarly causes a reverse, opening motion of anvil 140 upon distal rotation of closure trigger 112 at the opening of the instrument.

The anvil 140 comes to rest on the gap spacing pin 161 which forms the distal end of the cartridge 150. The gap spacing pin 161 causes the anvil 140 to be held roughly parallel to the cartridge 150. This has an advantage in providing an evenly spaced tissue compression. It also has an advantage of retaining tissue between the anvil 140 and the cartridge assembly 150 and keeps the tissue from being "oozed" out of the distal end of the instrument 100. In this way, the anvil 140 acts as a simply supported beam with an evenly distributed load.

Figure 8:
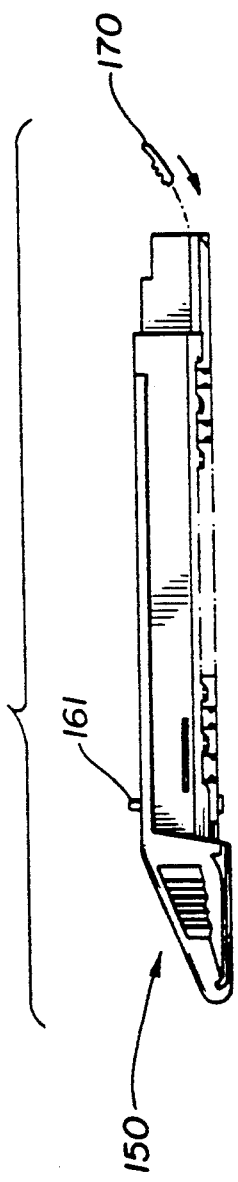
FIGS. 8 and 8a are side and bottom isolated views of a typical cartridge of the invention.
Figure 8A:
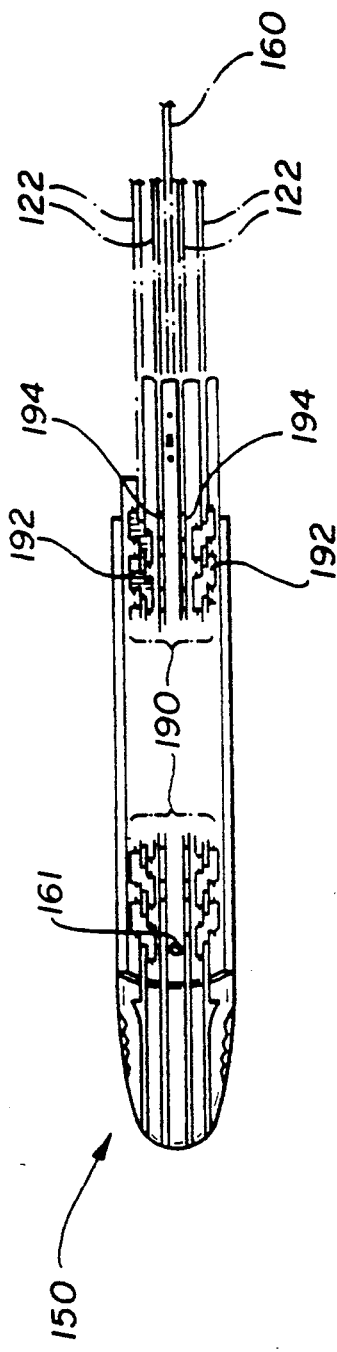
Figure 9:
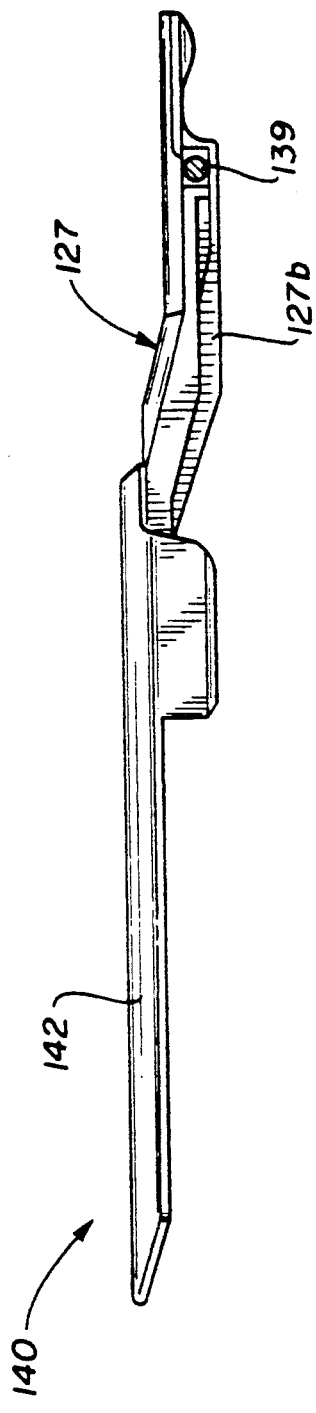
FIGS. 9 and 9a are side and bottom isolated views of the anvil of the invention.
Figure 9A:
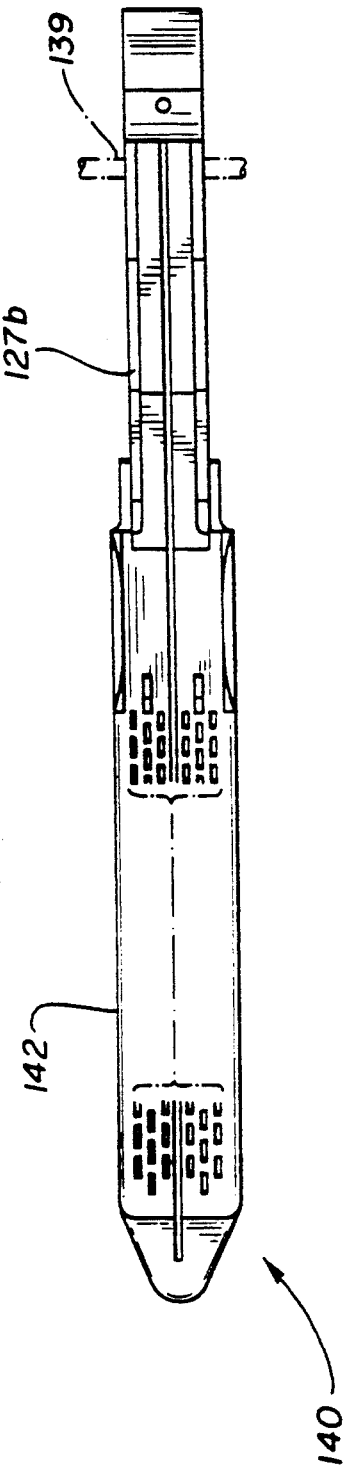

As better seen in FIGS. 8 and 8a, there is provided a cartridge assembly containing six rows 190 of staples. These staples are arranged with two pairs of pusher blocks 192 near the outside of the cartridge 150. Then, one pair of pusher blocks 194 is placed within the interior of cartridge 150. Thus, four wedges 122 pass through this cartridge 150, as better seen in FIG. 8a. Of course, knife 160 also passes through the center of cartridge 150.

The firing force to form the staples provides an additional concentrated, yet moving, load on the cantilever beam which forms the anvil 140. The tissue compression load and the staple forming forces tend to deflect the anvil 140 from the cartridge 150. The anvil therefore is preloaded, so that uneven staple forming is avoided. This preload is placed on the gap spacing pin 161 at the end of the cartridge 150 so that a load roughly equivalent to that of tissue compression force and staple forming force is countered. This makes the anvil 140 a simply supported beam, with loads at each end. This preload means that the anvil deflection caused by tissue compression and staple formation is compensated for by the reverse deflection caused by the gap spacing pin 161.

The disclosures of U.S. Pat. Nos. 4,633,861 and 4,633,874(Chow et al.) are incorporated by reference.

It can be seen in FIGS. 8, 11, 11a and 11b, that there is a unique lockout feature to this embodiment. As seen FIGS. 11a and 11b, the cartridge 150 contains a lockout member 170, having raised members 170a, which is better seen in FIG. 11. This lockout member 170 is provided within the cartridge so that is serves to lift the knife blade 160 over an obstructional block 172 placed within the stationary tube 130 of the mechanism. This causes the obstruction 172 to be cleared by the knife 160. Then, the knife 160 proceeds through the cartridge 150 for cutting. However, the knife has a notch 162 which engages the lockout member 170, and pushes it into opening 165 of cartridge 150. In this way, the lockout mechanism 170 operates at an even earlier time frame than previously disclosed locking mechanisms. It is important to realize that with the lockout mechanism described herein, the knife 160 is blocked even before entrance into cartridge 150.

As seen in FIG. 11b, after the knife 160 has been inserted into the cartridge 150, the raised members 170a of lockout member 170 have been caused to be captured below its cartridge retaining member 164 in opening 165, so that lockout member 170 becomes locked permanently within the cartridge 150. Therefore, after the knife 160 is retracted into the shaft 130, obstruction 172 now is level with the notch 166. In this way, there is no longer any clearance, between notch 166 and obstruction 172, as seen in FIG. 11b. In this way, if it is desired to refire this stapler, there is no possibility of knife hook 166 clearing the knife obstruction 172 in shaft 130. Therefore, refiring of this spent cartridge 150 is not possible.

If one were willing to accept any disadvantages which may be attendant, the stapler 100 may be modified as seen in FIG. 10a to allow cutting after the last staple has been fired. This is accomplished by removing member 166a adjacent to notch 166 using conventional methods, for example grinding or cutting. Or, knife 160 may be manufactured without notch 166 and member 166a.

Therefore, as seen from all the Figures previously listed above taken in conjunction with this Description, the following is a summary of the operation of the present invention. A fully loaded cartridge 150 is inserted into the stationary tube 130 at jaw 132. Thereafter, the instrument is inserted, closed, within a trocar and is opened, and gathers tissue between the anvil 140 and the cartridge assembly 150. The closure channel is operated by compressing the closure trigger 112. In this way, the closure trigger 112 causes all the closure mechanisms to rotate and move along an axis parallel to shaft 130. This causes the anvil 140 to encounter the gap setting pin 161 and capture tissue between the anvil 140 and cartridge 150. Thereafter, the anvil 140 is compressed onto the cartridge 150.

In the meantime, the clutch assembly of the firing trigger 114 has engaged the firing link 148, which is now operated. Tissue is stapled by rotation of the trigger 114. Also, simultaneously, the tissue is cut by the knife member 160. Once the firing stroke of the firing trigger 114 is completed, the rear safety button 131 must be released so that the mechanism can be reopened. The firing trigger 114 and closure trigger 112 are rotated to their original positions, and the lockout member 170 has caused the knife 160 to be obstructed from refiring. Thus the tissue is released, the mechanism retracted from the trocar tube, the cartridge 150 removed and a new cartridge inserted, and the stapler is again ready for firing.

As seen in FIGS. 12 through 20a, there is described an alternative preferred embodiment of the present invention. There is seen a stapler 5 which contains a handle portion 10, shaft portion 30, an anvil portion 40, cartridge assembly 50, rotational means 20, a first or closing trigger 12, a second or firing trigger 14, knife means 60, and firing wedges 54. The basic functions of all of these subassemblies are quite similar to those as described in the first preferred embodiment. However, there are certain aspects of the system which will now be more particularly described.

As seen in FIGS. 12 and 13, there is described a closure sheath 32 which is capable of camming the rear cam surface 43 of the anvil 40. This closure sheath 32 is operated by means of the closing trigger 12, attached thereto by means of a closure mechanism. The firing trigger 14 is similar to firing trigger 114 of the first embodiment, and is capable of activating the firing wedges 54 to expel staples from the stapling cartridge, while simultaneously activating knife means 60 to cut tissue between the two double rows of staples contained in cartridge assembly 50.

As will be better understood, there are certain aspects of the handle mechanism 10 which differ from the handle mechanism 110 of the first embodiment. As better seen in FIGS. 12a, 13, 14, 15 and 15a, the closing trigger 12 which operates the sheath 32 of the stapler is connected to firing trigger 14 by means of a two-piece linkage 34, 36. This linkage system 34, 36, is better seen in FIGS. 12a and 15a. Link 34 is connected by means of a pivot joint 45 to firing trigger 14 and is constrained to travel within an opening 45a in firing trigger 14. Link 34 is biased downward by spring means 33 connecting it to a boss in body plate 155. Link 36 is connected by means of a pivot joint 46 to closing trigger 12 and is constrained to travel within an opening 46a in trigger 12. Links 34 and 36 are constrained to move relative to each other due to link 36 nesting inside of a slot in link 34. The distance from pivot pin 13 to pivot joint 45 at which link 34 is connected to firing trigger 14 is proportionately smaller than that at which link 36 is connected to closing trigger 12. These differing distances or radii from pivot pin 13 cause the firing trigger 14 to rotate through a greater angle than that of the closing trigger 12 when the closing trigger mechanism is activated. This allows the firing trigger 14 to move from its initial position against the barrel position of the body to a position in which it can be easily activated for the firing operation. This occurs because link 36 is pulled upwards by the closing trigger 12 and, since it is nested in the slot 37 in link 36, link 34 pulls link 36 upward as well. The firing trigger 14 can be rotated into position against the grip portion of handle and continues to raise link 36. This additional travel of link 36 is accomplished since the slot in link 34 is longer than the body length of link 36 which is engaged in the slot 37.

Spring means 33 connected to link 34 causes link 34 to remain in contact with link 36 as well as to help return both links 34 and 36 and the respective triggers 12 and 14 to their original positions.

As seen in FIGS. 13, 16 16a, 17 and 17a, rear toggle member 44 has an extended portion 47 which rotates into a position so that it contacts the rear button release 31. The front toggle member 42 (connected at hole 12c to pin 12d and thereby to handle 12 at hole 12a), and rear toggle member 44 (connected at hole 12d to pin 12d and thereby to handle 12 at hole 12a) form the toggle linkage and are cammed into an over-center position, thus locking sheath 32 into a position which cams anvil 40 against cartridge assembly 50. Pushing the rear button release 31 exerts force on the elongated part 47 of the rear toggle 44 and rotates the rear toggle 44 past its over-center point. This allows spring 150a in conjunction with spring 33 and the linkage 34, 36 to pull the firing trigger 14, and closing trigger 12 into the "ready" position. Of course, both links 34, 36 of the trigger return act respectively on the triggers 14, 12. In this way, the stapler 5 is reset for firing as seen in FIG. 13.

As also seen in FIGS. 12a and 13, there is contained in this mechanism a safety pawl. The safety pawl 22 is capable of preventing motion of the firing mechanism of this embodiment of stapler·5 until closing trigger 12 has been fully moved to its closed position against the instrument hand grip 18 of handle portion 10. Safety pawl 22 is biased into its blocking position by means of spring 160a. Safety pawl 22 is moved out of the way of the firing mechanism through contact of latch 42a with notch 22a. That is, the safety pawl 22 becomes disengaged from its blocking position against the firing rack 25 which ultimately is operated by the firing trigger 14. Once the safety pawl 22 has been moved, firing can take place.

As better seen in FIGS. 12, 13, 16, 16a, 17 and 17a, closure is initiated by moving the closing trigger 12 against the instrument handle grip 18. This rotates the toggle linkage to its locked and over-center point, that is generally parallel with stapler shaft 30. This further causes sheath 32 to move in place within the stationary channel 30a which forms the shaft portion 30 of the mechanism. Thus, the toggle linkage which comprises both the rear toggle 44 and the front toggle 42, operates so that it moves the closure sheath 32 (which may operate as a camming collar) over the base 43 of the anvil 40. Thus, the closure mechanism now causes the anvil 40 and cartridge 50 to come in close proximity to each other.

At that point, the closure trigger 12 is held against the hand grip 18 and the firing trigger 14 is ready for actuation. The firing trigger 14 operates driver 89 connected to a belt 17, which is used to provide movement of firing rack 25 and driver rod 19. The belt 17 acts as a multiplier mechanism so that the firing trigger 14 pushes against the driver 89, seen in FIG. 13. Driver 89 thereafter causes the bottom portion 17c of belt 17 to move forward. Because one end of the belt 17a is fixed against the body of handle 18 of the stapler 5, and the other end of the belt 17b is attached to rack 25, this drives the knife means 60 and wedges 54 of the stapling mechanism forward. The motion of belt 17 causes motion of the driving rod 19 to be amplified as against the rotational motion of the firing trigger 14. Thus, this belt mechanism multiplies the firing distance travelled, so that stapling and cutting can take place.

The anvil portion 40 and cartridge assembly 50 operate very much as that of the first preferred embodiment. One difference, however, is that a preload is accomplished by tilting the anvil 40 and cartridge 50 toward each other at their distal ends to force distal closure to occur. As the proximal ends 40a of the anvil 40 and cartridge 50 are brought into a parallel position a preload is placed on the gap pin 61. This is better seen in FIGS. 13 and 18. The cam mechanism 43 on the rear of the anvil 40 is designed with a multiple angle. In this way, the steeper proximal portion of the angle allows faster closing of the anvil 40 against the cartridge assembly 50. Then the distal or more shallow angle is contacted by the closing sheath 32 when the instrument is nearly closed and experiencing high tissue load and high preload on the gap setting pin 61 found in the forwardmost position of the cartridge 50. These compound angles are specifically designed to give higher mechanical advantage when needed and faster closure and wider opening when needed.

As better seen in FIGS. 18, 18a, 19, 19a, 20, 20a and 20b, the lockout mechanism of the second embodiment is better seen when examining the cartridge 50 of the present system. There, it is seen as in FIG. 20, the lockout tab 71 is originally provided so that it is capable of lifting the knife means 60. In this way, the knife 60 moves forward and into the stapling cartridge 50. On the rearward motion of the knife, the forwardmost edge 63 of the knife mechanism 60 causes the lockout tab 71 to be rotated to become parallel with the stapling shaft 30. Thus, the knife 60 is made to move to a position lower in the stapling shaft 30. This causes the channel hook 59a which is contained in the stapling channel 59 to come into contact with the space 65 formed within the knife means 60. Thus, when it is now desired to move the knife mechanism forward, as will readily be appreciated, the hook 59 now catches on forward facing lip 66 of the knife means 60. Thus, the knife is incapable of moving forward and the stapler is now locked from firing through an already spent cartridge 50.

Of course, as seen in FIGS. 18 and 18a, there are disclosed four rows, that is two double rows 92 of staples in the cartridge 50. These rows 92 are actuated by pusher blocks 94 contacting wedges 54. Knife 60 passes through the center of rows 92.

In operation, the stapler of this second embodiment also performs similar functions. There is similar stapler safety, and clamping as that of the first preferred embodiment, and the firing and cutting of tissue accomplished all in the same order. Stapler lockout is accomplished afterwards by retraction of the knife mechanism.

This invention has been described in connection with two particularly preferred embodiments. However, it is to be understood that one may accomplish the invention in a number of substantially similar ways without departing from the scope of the invention. Accordingly, it is to be understood that the invention is to be better realized from the attached claims and their equivalents.

What is claimed is:

1. An endoscopic surgical tissue fastening instrument comprising:
   a tissue fastening portion;
   a handle portion having a handle; and
   an elongated shaft portion connecting said tissue fastening portion and said handle portion,
   wherein said tissue fastening portion contains a cartridge portion having a plurality of fasteners arranged to be placed into tissue and an anvil portion arranged to clamp tissue between said anvil portion and said cartridge portion so as to permit the firing of said tissue fasteners into tissue; and
   said cartridge portion and anvil portion pivotable one with respect to the other;
   and said handle portion containing a closure trigger and a firing trigger, said closure trigger remotely connected to said anvil portion, said closure trigger capable of causing said anvil portion to pivot so as to bring said anvil portion into proximity with said cartridge portion, and said firing trigger connected to said cartridge portion and capable of firing said fasteners from said cartridge portion into said tissue so as to fasten said tissue, and
   wherein said firing trigger and said closure trigger are pivotable with respect to said handle, and said closure trigger having: an initial position, and a clamping position pivotally displaced from said initial position; and said firing trigger having: an initial position pivotally displaced from said closure trigger initial position, an intermediate position pivotally displaced from said firing trigger initial position, and a final position pivotally displaced from said intermediate position; and further including engagement means on said closure trigger for actuating said firing trigger from its initial position to its intermediate position during motion of said closure trigger from its initial position to its clamping position.

2. The instrument of claim 1 further containing a knife in said tissue fastening portion, said knife further connected to said firing trigger, and said knife capable of severing tissue contained between said cartridge portion and said anvil portion.

3. The instrument of claim 1 further containing clutch means in said handle portion, said clutch means causing engagement of said firing trigger with said cartridge portion when said firing trigger has moved to said intermediate position so that said firing means is thereafter able to cause firing of said tissue fasteners from said cartridge portion during motion of said firing trigger from said intermediate position to said final position.

4. The instrument of claim 1 wherein said closure trigger pivots from said initial position to said clamping position, wherein said clutch means engages said firing trigger, and said closure trigger pivoting through an arc of between 25° and 50° from said initial position to said clamping position.

5. The instrument of claim 4 wherein said engagement means pivots said firing trigger to through an arc between about 30° to 60° from its initial position to its intermediate position during motion of said closure trigger from its initial position to its clamping position.

6. The instrument of claim 2 further comprising a lockout mechanism which contacts said knife during motion of said knife between said tissue fastening portion and said anvil portion such that said knife moves said lockout mechanism to a position wherein said firing trigger is prevented from being refired.

7. The instrument of claim 6 wherein staples are contained in a cartridge forming said cartridge portion and said lockout mechanism is placed in said cartridge.

8. The instrument of claim 7 further comprising an obstructing mechanism contained on said shaft portion, and said obstructing mechanism contacting said knife after said lockout mechanism has been actuated on said cartridge.

9. The instrument of claim 7 wherein lockout mechanism comprises a tab on said cartridge portion, said tab contacting said knife during motion of said knife between said tissue fastening portion and said anvil portion, such that said tab moves from an initial position to a blocking position and said knife prevented from being moved when said tab is in said blocking position.

10. The instrument of claim 3 wherein said anvil portion is further connected to anvil shifting means, and said anvil shifting means contacting said shaft portion, wherein upon movement of said closure trigger to said clamping position, said anvil shifting means guides said anvil portion first from a position apart from said cartridge portion to a position parallel with said cartridge portion and further to a position in close proximity with said cartridge portion.

11. The instrument of claim 10 wherein said anvil portion is preloaded when in proximity of said cartridge portion.

12. The instrument of claim 3 further comprising a pawl, wherein said firing trigger is prevented from engaging with said tissue fastening portion by said pawl.

13. The instrument of claim 4 further containing multiplier means connecting said closure trigger and said firing trigger, such that the angular arc of travel of said closure trigger from said initial position to said clamping position causes said multiplier means to produce a pivoting motion in said firing trigger through a greater angular arc than passed through by said closure trigger.

14. The instrument of claim 13 wherein said multiplier means is a radially operated two part linkage, said linkage causing said firing trigger and said closure trigger to rotate simultaneously along different circumferential axes.

15. The instrument of claim 14 wherein said clutch means simultaneously disengages said closure trigger from said firing trigger when said closure trigger is in said clamping position and said firing trigger is engaged by said clutch means to said tissue fastening portion.

16. The instrument of claim 4 further containing reset means connected to said handle portion and said closure trigger, said reset means actuated when said closure trigger is in said clamping position, and said reset means including a push button attached to spring means, and said push button actuating said spring means so that said spring means returns said closure trigger from its clamping position to its initial position and similarly moves said anvil portion to pivot out of proximity with said cartridge portion.

17. An endoscopic surgical tissue fastening instrument comprising:
   a tissue fastening portion;
   a handle portion having a handle; and
   an elongated shaft portion connecting said tissue fastening portion and said handle portion,
   wherein said tissue fastening portion contains a cartridge portion having a plurality of fasteners arranged to be placed into tissue and an anvil portion arranged to clamp tissue between said anvil portion and said cartridge portion so as to permit the firing of said tissue fasteners into tissue; and said cartridge portion and anvil portion pivotable one with respect to the other;

and said handle portion containing a closure trigger and a firing trigger, said closure trigger remotely connected to said anvil portion, said closure trigger capable of causing said anvil portion to pivot so as to bring said anvil portion into proximity with said cartridge portion, and said firing trigger connected to said cartridge portion and capable of firing said fasteners from said cartridge portion into said tissue so as to fasten said tissue, and wherein said firing trigger and said closure trigger are pivotable with respect to said handle, and said closure trigger having: an initial position, and a clamping position pivotally displaced from said initial position; and said firing trigger having: an initial position pivotally displaced from said closure trigger initial position, an intermediate position pivotally displaced from said firing trigger initial position, and a final position pivotally displaced from said intermediate position: and further including engagement means on said closure trigger for actuating said firing trigger from its initial position to its intermediate position during motion of said closure trigger from its initial position to its clamping position; and further containing clutch means in said handle portion, said clutch means causing engagement of said firing trigger with said cartridge portion when said firing trigger has moved to said intermediate position so that said firing means is thereafter able to cause firing of said tissue fasteners from said cartridge portion during motion of said firing trigger from said intermediate position to said final position.

18. An endoscopic surgical tissue fastening instrument comprising:

a tissue fastening portion;

a handle portion having a handle; and an elongated shaft portion connecting said tissue fastening portion and said handle portion, wherein said tissue fastening portion contains a cartridge portion having a plurality of fasteners arranged to be placed into tissue and an anvil portion arranged to clamp tissue between said anvil portion and said cartridge portion so as to permit the firing of said tissue fasteners into tissue; and said cartridge portion and anvil portion pivotable one with respect to the other;

and said handle portion containing a closure trigger and a firing trigger, said closure trigger remotely connected to said anvil portion, said closure trigger capable of causing said anvil portion to pivot so as to bring said anvil portion into proximity with said cartridge portion, and said firing trigger connected to said cartridge portion and capable of firing said fasteners from said cartridge portion into said tissue so as to fasten said tissue, and wherein said firing trigger and said closure trigger are pivotable with respect to said handle, and said closure trigger having: an initial position, and a clamping position pivotally displaced from said initial position; and said firing trigger having: an initial position pivotally displaced from said closure trigger initial position, an intermediate position pivotally displaced from said firing trigger initial position, and a final position pivotally displaced from said intermediate position: and further including engagement means on said closure trigger for actuating said firing trigger from its initial position to its intermediate position during motion of said closure trigger from its initial position to its clamping position; and further containing multiplier means connecting said closure trigger and said firing trigger, such that the angular arc of travel of said closure trigger from said initial position to said clamping position causes said multiplier means to produce a pivoting motion in said firing trigger through a greater angular arc than passed through by said closure trigger.

19. The instrument of claim 18 wherein said multiplier means is a radially operated two part linkage, said linkage rotating said firing trigger and said closure trigger simultaneously along different circumferential axes.

20. The instrument of claim 18 further containing a clutch means in said handle portion, said clutch means causing engagement of said firing trigger with said cartridge portion when said firing trigger has moved to said intermediate position so that said firing means is thereafter able to fire said tissue fasteners from said cartridge position during motion of said firing trigger from said intermediate position to said final position.

21. The instrument of claim 18 further containing a knife in said tissue fastening portion, said knife further connected to said firing trigger, and said knife capable of severing tissue contained between said cartridge portion and said anvil portion.

22. The instrument of claim 21 further comprising a lockout mechanism which contacts said knife during motion of said knife between said tissue fastening portion and said anvil portion such that said knife causes said lockout mechanism to move to a blocking position wherein lockout mechanism prevents said firing trigger from being refired.

* * * * *